US007550558B2

(12) United States Patent
Leite et al.

(10) Patent No.: US 7,550,558 B2
(45) Date of Patent: Jun. 23, 2009

(54) ANTIMICROBIAL PEPTIDES AND METHODS FOR IDENTIFYING AND USING SUCH PEPTIDES

(75) Inventors: Adilson Leite, Sao Paulo (BR); Urara Kawazoe, Sao Paulo (BR); Paulo Arruda, Sao Paulo (BR); Arnaldo da Silva Junior, Sao Paulo (BR)

(73) Assignee: Fundacao de Ampara a Pesquiso do Estado de Sao Paolo (FAPESP), Sao Paolo (BR)

( * ) Notice: Subject to any disclaimer, the term of this patent is extended or adjusted under 35 U.S.C. 154(b) by 308 days.

(21) Appl. No.: 09/870,498

(22) Filed: Jun. 1, 2001

(65) Prior Publication Data

US 2003/0148397 A1 Aug. 7, 2003

(51) Int. Cl.
*C07K 7/00* (2006.01)
*A61K 38/04* (2006.01)
*A61K 38/00* (2006.01)
*C40B 40/10* (2006.01)
*C40B 30/06* (2006.01)
*C40B 40/02* (2006.01)

(52) U.S. Cl. .................. 530/327; 530/305; 530/328; 514/2; 514/14; 514/15; 506/18; 506/10; 506/14

(58) Field of Classification Search .............. 435/32, 435/29, 7.1; 530/300, 305, 325, 327; 506/10, 506/14, 18; 514/2, 14, 15
See application file for complete search history.

(56) References Cited

U.S. PATENT DOCUMENTS

| 4,710,377 | A | * | 12/1987 | Schenkel et al. | ............... 424/88 |
| 5,324,716 | A | * | 6/1994 | Selsted et al. | ................. 514/14 |
| 5,447,914 | A | * | 9/1995 | Travis et al. | .................. 514/16 |
| 5,766,624 | A | * | 6/1998 | Janoff et al. | ................. 424/450 |
| 5,994,308 | A | * | 11/1999 | Lawyer et al. | ................ 514/15 |
| 6,040,435 | A | * | 3/2000 | Hancock et al. | ............. 536/23.1 |
| 6,262,243 | B1 | * | 7/2001 | Lawyer et al. | ............. 526/23.1 |
| 6,372,888 | B1 | * | 4/2002 | De Samblanx et al. | ...... 530/350 |
| 6,497,870 | B1 | * | 12/2002 | Ford et al. | ................. 424/85.2 |
| 6,835,536 | B2 | * | 12/2004 | Krieger et al. | ................. 435/5 |
| 7,214,766 | B2 | * | 5/2007 | Everett et al. | ............... 530/300 |

FOREIGN PATENT DOCUMENTS

| EP | 1262556 A2 | * | 12/2002 |
| WO | WO 99/36081 |  | 7/1999 |
| WO | WO99/37678 | * | 7/1999 |
| WO | WO-00/18951 |  | 4/2000 |
| WO | WO 00/23465 |  | 4/2000 |
| WO | WO 02/34789 |  | 5/2002 |
| WO | WO 02/090503 |  | 11/2002 |

OTHER PUBLICATIONS

§ Selsted, M.E. et al., Ondolicifdin, a novel Bactericidal tridecapeptide Amide from Neutrophils. 1992. The Journal of Biological Chemistry, vol. 272, pp. 4292-4295.*

Charles S. Gasser. 1996, U. C. Davis, Biological Sciences, Amino Acid Properties. Printed from http://www.mcb.ucdavis.edu/courses/bis 102/AAProp.html on Oct. 25, 2007.*
Wikipedia, modified Dec. 30, 2008, at 01:04, http://en.wikipedia.org/wiki/Antimicrobial, printed on Jan. 2, 2009.*
Nagpal et al. 1999. Structure-Function Analysis of Tritrypticin, an Antibacterial Peptide of Innate Immune Origin. Journal of Biological Chemistry, vol. 274, No. 33, pp. 32296-32304.*
Barry, M.A. et al. Toward cell-targeting gene therapy vectors: Selection of cell-binding peptides from random peptide-presenting phage libraries. Nature Medicine, 2(3), pp. 299-305 (1996).
Doorbar, J. & Winter, G. Isolation of a peptide antagonist to the thrombin receptor using phage display. J. Mol. Biol., 244, pp. 361-369 (1994).
Ahmad, I. Liposomal entrapment of the neutrophil-derived peptide indolicidin endows it with in vivo antifungal activity. Biochim Biophys Acta, 1237, pp. 109-114 (1995).
Lawyer, C. et al. Antimicrobial activity of a 13 amino acid tryptophan-rich peptide derived from a putative porcine precursor protein of a novel family of antibacterial peptides. FEBS Letters, 390, pp. 95-98 (1996).
Subbalakshmi, C. et al. Requirements for antibacterial and haemolytic activities in the bovine neutrophil derived 13-residue peptide indolicidin, FEBS Letters, 395, pp. 48-52 (1996).
Subbalakshmi, C. et al. Antibacterial and haemolytic activities of single tryptophan analogs of indolicidin. Biochemical and Biophysical Research Communications, 274, pp. 714-746 (2000).
Selsted, M.E. et al. Indolicidin, a novel tridecapeptide amide from neutrophils. J. Biol. Chem., 267, pp. 4292-4295 (1992).
Falla, T.J. et al. Mode of action of the antimicrobial peptide indolicidin. J. Biol. Chem., 271, pp. 19298-19303 (1996).
Blondelle, S.E. & Houghten, R.A. Novel antimicrobial compounds identified using synthetic combinatorial library technology. TIBTECH, 14, pp. 60-65 (1996).
Martin, A. et al. Evaluation of the effect of peptidyl membrane-interactive molecules on avian coccidian. Parasitol. Res., 85, pp. 331-336 (1999).
Da Silva A, Jr. et al. "Avian Anticocidial Activity of a Novel Membrane-Interactive Peptide Selected from Phage Display Libraries", Molecular and Biochemical Parasitology, vol. 120, Mar. 2002 (20202-03), pp. 53-60, XP002258130.
Christensen D. J. et al. "Phage Display For Target-Based Antibacterial Drug Discovery", Drug Discovery Today, vol. 6, No. 14, Jul. 2001, XP002258131.
Benson R.E.et al. "Intercellular Validation of Surrogate Ligands For Antimicrobial Drug Discovery", Abstract of the General Meeting of the American Society for Microbiology, vol. 101, May 2001, pp. 536-537, XP009019300.
Jolivet-Reynaud C. et al. "Localization of Hepatitis B Surface Antigen Epitopes Present on Variants and Specifically Recognised by Anti-Hepatitis B Surface Antigen Monoclonal Antibodies", Journal of Medical Virology, vol. 65, Oct. 2001, pp. 241-249, XP002195005.
Tinoco I.W. et al "NMR Structure of PW2 Bound to SDS Micelles", The Journal of Biological Chemistry, vol. 277, No. 39, 2002, pp. 36351-36356, XP002269890.
Database EMBL 'Online! 12 aa, Jun. 21, 2002 , "Sequence 2 from patent WO 02/34789", XP002269891, retrieved from EBI Database accession No. AX429444 L document cited to provide infromation on the relevant sequence disclosed in WO 02/34789.

* cited by examiner

*Primary Examiner*—Jon P Weber
*Assistant Examiner*—Kailash C Srivastava
(74) *Attorney, Agent, or Firm*—Fulbright & Jaworski LLP

(57) ABSTRACT

This invention relates to a method for identifying peptides having antimicrobial activity and to the antimicrobial peptides identified thereby and methods for their use.

20 Claims, 7 Drawing Sheets

| Library | Sequence | Incidence |
|---|---|---|
| Ph.D.-12 | HPLKQYWWRPSI----- | 22/26 |
| Ph.D.-12 | ----PIWWKHSGGPIL- | 1/26 |
| Ph.D.-12 | -----YWWRDAPVSQGR | 1/26 |
| Ph.D.-12 | SYPTDKWWIKPG----- | 1/26 |
| Ph.D.-7 | ----VQWWRPT------ | 7/15 |
| Ph.D.-7 | -----NWWRPLP----- | 1/15 |
| Ph.D.-7 | ----GKWWVFD------ | 1/15 |
| Ph.D.-7 | -VPTKPWW--------- | 1/15 |
| Ph.D.-C7C | -----PWWKTSK----- | 6/15 |
| Ph.D.-C7C | -----PWWKASS----- | 1/15 |
| Ph.D.-C7C | ---TPTWWRT------- | 1/15 |
| Ph.D.-C7C | ---APTWWKS------- | 1/15 |
| Ph.D.-C7C | ------WWTSASR--- | 1/15 |
| Ph.D.-C7C | ---SARWWQP------- | 1/15 |

FIG.1

ANTIMICROBIAL PEPTIDES AND METHODS FOR IDENTIFYING AND USING SUCH PEPTIDES

FIELD OF THE INVENTION

The present invention relates to a method for identifying peptides having antimicrobial activity, the peptides identified by the method and to methods of using such peptides.

BACKGROUND OF THE INVENTION

Since the introduction of penicillin in the 1940s, the use of antibiotics has improved the expectancy and quality of life. Unfortunately however, the effectiveness of most antibiotics has declined due to the development of resistant microbial strains. A factor that has contributed to the development of such antibiotic resistant strains has been the chronic overuse of these drugs by the general population.

Recently, it has been recognized that natural antimicrobial peptides participate in the innate immune systems of animals and plants. Most of these antimicrobial peptides are cationic amphipathic molecules composed of 12 to 45 amino acid residues. These peptides act by permeabilizing the membrane forming pores and eventually cause cell lysis. It has been demonstrated that some of these peptides, as well as synthetic ones, exhibit activity against protozoan parasites (Jaynes et al., "In vitro cytocidal effect of novel lytic peptides on *Plasmodium falciparum* and *Trypanosoma cruzi*", *FASEB J.*, 2: 2878-2883 (1988); Arrowood et al., "In vitro activities of lytic peptides against the sporozoites of *Cryptosporidium parvum*", *Antimicrob. Agents Chemother*, 35:224-227 (1991); Aley et al., "Killing of *Giardia lamblia* by cryptdins and cationic neutrophil peptides", *Infect. Immun.* 62 (12): 5397-5403 (1994); Barr et al., "Activity of lytic peptides against intracellular *Trypanossoma cruzi* amastigotes in vitro and parasitemias in mice", *J. Parasitol.*, 81: 974-978 (1995), and; Martin et al., "Evaluation of the effect of peptidyl membrane-interactive molecules on avian coccidian", *Parasitol. Res.*, 85: 331-336(1999)). This mode of action endows antimicrobial peptides with broad activity against many bacteria, fungi and protozoa species. Unfortunately, heretofore naturally occurring antimicrobial peptides, e.g., indolicidin and tritrpticin, have had adverse effects on host cells susceptible to infection by the microorganisms (Hancock & Lehrer, "Cationic peptides: a new source of antibiotics", *Trends Biotech.* 16: 82-88 (1998); Andreu & Rivas, "Animal antimicrobial peptides: An overview", *Peptide Science* 47, 415-433 (1998)) and thus possess an inherent limitation as therapeutic agents. In addition, the effects of indolicidin and tritipticin are not universal and thus additional peptides with specificity for a broader range of pathogenic organisms or specificity for particular microorganisms are needed.

Accordingly, it is desirable to identify peptides that possess high specificity for pathogenic microorganisms, but have a low toxicity to host cells susceptible to infection by the pathogenic microorganisms. Such antimicrobial peptides would be useful for inhibiting infection, proliferation and viability of pathogenic microorganisms. It is also desirable to develop a method for assaying peptides for antimicrobial activity.

SUMMARY OF THE INVENTION

This invention relates to antimicrobial peptides that are specific for a variety of microorganisms, but are non-toxic or have low toxicity to animal and plant cells susceptible to infection by the microorganism.

This invention relates to a peptide having a specificity for a pathogenic microorganism, wherein the peptide consists of about 10 to about 50 amino acids, preferably 12 to about 45 amino acids, more preferably about 12 to about 35 amino acids and most preferably 12 to about 25 amino acids, wherein of the peptide comprises 10 to 12 contiguous amino acids of which seven out of the 10 to 12 amino acids are hydrophobic, three out of the 10 to 12 contiguous amino acids are basic and at least one out of the 10 to 12 contiguous amino acid is histidine (His), glutamine (Glu) or serine (Ser), with the proviso that at least two of the seven hydrophobic amino acids are adjacent tryptophans (Trp). The hydrophobicity scales used herein are as described in Jones, *J. Theor. Biol*, 50:167-183 (1975); Hoop and Woods, "Prediction of protein antigenic determinants from amino acid sequences" *Proc Natl Acad Sci USA* 78:3824 (1981) and Sweet & Eisenberg, "Correlation of sequence hydrophobicities measures similarity in three-dimensional protein structure," *J Mol Biol* 171(4): 479-88 (1983) (OHM scale, optimal matching hydrophobicity scale)(all incorporated herein by reference) wherein tyrosine is considered a hydrophobic residue. The OHM scale is based on the likelihood of a given amino acid to be replaced by another hydrophobic or "buried" amino acid.

In one embodiment, the peptide consists of 10 to 12 contiguous amino acids wherein seven of the 10 to 12 contiguous amino acids that are hydrophobic, three of the 10 to 12 contiguous amino acids that are basic and at least one of the 10 to 12 contiguous amino acids is histidine (His), glutamine (Glu) or serine (Ser), with the proviso that at least two of the seven hydrophobic amino acids are adjacent tryptophans (Trp). Preferably the peptide comprises the sequence HPLKQYW-WRPSI (SEQ ID NO:1), or a conservative variant thereof. More preferably the peptide consists of the amino acid sequence of SEQ ID NO:1. Preferably the peptide has an isoelectric point ("pI" hereinafter) of about 10.

Preferably the peptides of this invention exhibit low toxicity to animal and plant cells as compared to the toxic effects of the peptides on the pathogenic microorganism used to select the peptide, e.g., a protozoa, bacteria or fungus. Toxicity may be determined by assaying the amount of host cell death caused by the minimum concentration of peptide that causes 90-100% cell death of the pathogenic microorganism after incubation with the peptide for about 1 hour at 37° C. Peptides of this invention which exhibit low toxicity to animal and plant cells cause, e.g., less than about 30% death of the host cells when incubated with the minimum concentration of peptide that causes about 90-100% cell death of the pathogenic microorganism after incubation with the peptide for about 1 hour at 37° C. More preferably peptides exhibiting low toxicity cause less than about 20% death of the host cells and most preferably the amount of host cell death caused by the peptide is insignificant as compared to host cells that were not contacted with the peptide.

Also encompassed by the present invention are conservative variants of the peptide, as well as analogs of the peptide, discussed infra. Such variants include, e.g., those containing substitutions of amino acid residue(s) of SEQ ID NO:1 with other residues that are functionally equivalent, resulting in a conservative amino acid substitution. The substitutions may be made based on conserving charge and topological structure. Bordo & Argos, *J. Mol. Biol.*, 217:721-729 (1991)(incorporated herein by reference) also present rules for conservative substitution based on exchange matrices representing natural substitutions. The matrices were obtained by comparison of known conserved three-dimensional protein structures. The rules presented by Bordo & Argos are summarized in FIG. 6. For example, Lys may substitute Arg and vice versa such that a positive charge may be maintained; Glu may substitute Asp and vice versa such that a negative charge may be maintained, and; Ser may substitute Thr such that a free —OH can be maintained.

Examples of analogs of the peptides described herein include, but certainly are not limited to, an amidated form of a peptide having an amino acid sequence of SEQ ID NO:1 or a carboxymethylated form of a peptide having an amino acid of SEQ ID NO:1. A peptide comprising SEQ ID NO: 1 may also comprise amino acids that provide for its cyclization or may be labeled. Particularly useful labels are described infra.

Analogs of the peptides of this invention also include peptidomimetic compounds having substantially the same antimicrobial activity as PW2. Methods for the production of peptidomimetic compounds are known to those of skill in the art and are reviewed in Al-Obeidi et al., *Mol Biotechnol* 9:205-223 (1998)(incorporated herein by reference).

This invention also relates to compositions comprising the peptides, and to compositions comprising the peptides and one or more additional antimicrobial agents. The invention further relates to conjugates of the peptide and a conjugation partner, and to compositions comprising the conjugates. Such partners may be, e.g., enzymes and cytotoxic or cytolytic agents.

The present invention also relates to an antibody specific for an isolated peptide comprising the amino acid sequence of SEQ ID NO:1 or a conservative variant thereof. An antibody of the present invention can be a polyclonal antibody, a monoclonal antibody, a chimeric, dimeric, trimeric, heteromeric or single chain antibody. Moreover, the antibody of the present invention can be detectably labeled. Such antibodies would have a variety of uses, e.g., for isolating, purifying or quantitating the peptides of this invention.

The present invention further relates to nucleic acid molecules that encode the peptides of this invention, such as, e.g., peptides that comprise the amino acid sequence of SEQ ID NO:1, or conservative variants thereof. The nucleic acid molecules of this invention may be labeled. The nucleic acid molecule may also be in operable linkage with a promoter.

Moreover, the present invention relates to cloning vectors and expression vectors comprising the nucleic acid molecule of this invention. Cloning vectors are useful for producing multiple copies of the isolated nucleic acid molecule. Expression vectors comprise the nucleic acid molecules of this invention in operable linkage with a promoter. Those of skill in the art appreciate that many suitable vectors are readily available, for example, a mammalian virus, a bacteriophage, e.g., a lambda phage, or a plasmid, e.g., a pBR322, a pUC, a pGEX, pMal-C, or pFLAG.

The peptides of this invention may be joined together into a polypeptide comprising multiple peptides of this invention. The polypeptides may form a "polytope." Polytopes are groups of two or more peptides. These peptides can be joined together directly or via the use of linker sequences. See, e.g., Thompson et al., *PNAS*, 92(13):5845-5849 (1995)(incorporated herein by reference), teaching the direct linkage of relevant epitopic sequences. The linker sequences may comprise recognition sites for proteolytic enzymes which would digest the polypeptide into its component peptides. For example, the linker may comprise a recognition site for a protease specific for a particular target organ or tissue, e.g., avian gut.

In one embodiment the polytopes may be designed to be immunogenic or immune stimulating to generate antibodies. The use of polytopes for generating antibodies and cellular immunity is well known. See, e.g., Gilbert et al., *Nat. Biotechnol.*, 15(12):1280-1284 (1997): Thomson et al., supra; Thomson et al., *J. Immunol.*, 157(2):822-826 (1996), and; Tam et al., *J. Exp. Med.*, 171(1):299-306(1990), all incorporated herein by reference. The Tam reference in particular discloses polytopes prepared from short peptides that are presented on the surface of cells in complex with an MHC molecule which are recognized by cytolytic T cells. Tam et al. demonstrate that the polytopes, when digested, yielded peptides which can be and are presented by MHCs. Thus this approach can be used, e.g., to generate polypeptides which may be digested to release the particular peptides of this invention or may be used in determining how many peptides can be joined in a polytope and still bind to pathogenic organisms, or could be used to determine the antimicrobial activity of different combinations of peptides.

This invention further relates to a method for inhibiting proliferation or viability of a microorganism, e.g., a fungus, such as, *Candida albicans* or *Aspergillus nidulans*, or a protozoa, e.g., a sporozoite of *E. acervulina* or *E. tenella*, in an environment capable of sustaining such survival or growth. For example, an effective amount of a peptide of this invention is administered to the environment capable of sustaining the survival or growth of a microorganism, e.g, a food product, an animal feed or a water supply, wherein the effective amount is sufficient to inhibit proliferation or viability of the microorganism. Preferably the peptide comprises the amino acid sequence of SEQ ID NO:1 or a conservative variant thereof. More preferably the peptide consists of the amino acid sequence of SEQ ID NO:1 or a conservative variant thereof. The methods of this invention also relate to preventing a microorganism, e.g., a fungus, such as, *Candida albicans* or *Aspergillus nidulans*, or a protozoa, e.g., a sporozoite of *E. acervulina* or *E. tenella*, from infecting and proliferating in an organism. For example, an effective amount of a peptide of this invention may be administered to the organism prophylactically, during or subsequent to infection, wherein the effective amount is sufficient to inhibit infection or proliferation of the microorganism in the organism. Preferably the peptide comprises the amino acid sequence of SEQ ID NO:1 or a conservative variant thereof. More preferably the peptide consists of the amino acid sequence of SEQ ID NO:1 or a conservative variant thereof.

Thus a further aspect of this invention is a method to produce plants resistant to pathogenic organisms, e.g., bacteria, fungi and insects, by transforming plant cells with a nucleic acid molecule that encodes the peptides of this invention and regenerating and identifying transgenic plants that produce the peptides of this invention. Preferably the transgenic plants display resistance to the pathogenic organisms. Also an aspect of this invention are the transformed plant cells and transgenic plants that produce the peptides of this invention.

Those of skill in the art are well aware of a variety of methods for transforming plant cells and regenerating transgenic plants from those cells. For example, plant cells may be transformed by using any suitable DNA transfer technology, such as, e.g., Agrobacterium mediated transfection, particle or microprojectile bombardment (U.S. Pat. No. 5,100,792, EP-A-444882, EP-A-434616, Altpeter et al., *Plant Cell Rep.*, 16:12-17 (1996) or Klein et al., *Nature*, 327:70-73 (1987), incorporated herein by reference), microinjection(WO92/09696, WO 94/00583, EP 331083, EP 175966, Green et al., *Plant Tissue and Cell Culture*, Academic Press (1987), incorporated herein by reference), electroporation (EP 290395, WO 8706614 incorporated herein by reference), liposome mediated DNA uptake (e.g., Freeman et al., *Plant Cell Physiol.*, 29:1353 (1984), incorporated herein by reference), the vortexing method (e.g., Kindle, *PNAS USA*, 87:1228

(1990), incorporated herein by reference), silicon carbide fibers (see, e.g., U.S. Pat. No. 5,302,523, incorporated by reference) and other forms of direct DNA uptake (DE 4005152, WO 9012096, U.S. Pat. No. 4,684,611, incorporated herein by reference). For a review of physical methods for the transformation of plant cells see, e.g., Oard, *Biotech. Adv.*, 9:1-11 (199 1)(incorporated herein by reference).

Those of skill in the art appreciate that different methods may be used to regenerate transgenic plants from transformed cells in culture. A plant may be regenerated, e.g., from single cells, callus tissue, leaf discs, and immature or mature embryos, hypocotyls and cotyledons, as is standard in the art. Almost any plant, e.g., rice, wheat, corn, oat, barley, sorghum, legumes, and woody species can be entirely regenerated from cells, tissues and organs of the plant. The generation of fertile transgenic plants has been achieved in the cereals, e.g., rice, maize, wheat, oat, and barley (reviewed in Shimamoto, K., *Current Opinion in Biotechnology*, 5:158-162 (1994); Vasil et al., *Bio/Technology*, 10:667-674, (1992); Vain et al., *Biotechnology Advances*, 13:4:653-671, (1995); Vasil, *Nature Biotechnology*, 14, page 702 (1996)). Available techniques are also reviewed in Vasil et al., "Cell Culture and Somatic Cell Genetics of Plants", Vol I, II, and III, *Laboratory Procedures and Their Applications*, Academic Press, (1984), Weissbach and Weissbach, *Methods for Plant Molecular Biology*, Academic Press, (1989) and also Christou, *Plant Mol. Biol.* 163: 39-44 (1997); Cao et al., *Plant Gene Transfer, UCLA Symposium Molecular and Cellular Biology*, 129:21-33 (1990), D'Halluin et al., *Plant Cell*, 4:1495-1505 (1992), Lowe et al., *Bio/Technology*, 13:677-682 (1995) and Osusky et al., *Nat. Biotechnology*, 18:1162-1166 (2000)(all incorporated herein by reference).

An additional aspect of this invention is a composition comprising the peptides of this invention for administration to a host organism e.g., a mammal, a bird, or plant in need thereof, wherein the peptide is administered in an amount that is effective for inhibiting the ability of the microorganism to infect the host or to proliferate within the host.

The invention also relates to methods for isolating and identifying peptides (i) that are specific for pathogenic microorganisms and (ii) that have antimicrobial activity. In one embodiment the method comprises contacting a preselected microorganism with a plurality of peptides, allowing the peptides to bind to the microorganism, isolating the microorganisms with bound peptides, identifying the bound peptides and then assaying the peptides for antimicrobial activity.

One of ordinary skill in the art can readily determine whether the peptide binds to the microorganism using routine laboratory techniques, e.g., separating the peptide-bound microorganism from the unbound free microorganisms and then eluting the bound peptide from the microorganism with a composition that causes the dissociation of the microorganism and peptide. Alternatively, the microorganism can be affixed to a solid support, and then contacted with the peptides to be screened. Subsequently, the microorganism is removed from the solid support and examined for bound peptide. The bound peptide may also be removed from the microorganism. Particular examples of solid substrates include, e.g., a petri-plate, glass or silicon beads, etc.

In one embodiment of the invention, the antimicrobial activity of the peptide is assayed by contacting a microorganism with the peptide, and then examining the surface of the microorganism for damage, wherein damage to the surface is indicative of antimicrobial activity. The method may comprise removing bound peptide from the microorganism prior to examining the surface for damage. In addition, the method may comprise a step for determining whether the isolated peptide binds to the outer surface of the microorganism.

A plethora of methods for examining the surface of the microorganism for damage are available to the skilled artisan. For example, the microorganism may be examined for damage under a light microscope or an electron microscope. Alternatively, the microorganism can be contacted with an agent that cannot cross an undamaged membrane, e.g., Sytox Green, propidium iodide, and dimeric and monomeric cyanine dyes and assayed for the presence of the agent within the microorganism. The agent's presence within the microorganism is indicative of damage to the microorganism's membrane, and thus, antimicrobial activity.

Another method for assaying for membrane damage involves contacting the microorganism, with or without peptide, with an agent that crosses the membrane of the microorganism and is subsequently processed within the cytosol to form a product that is unable to cross an undamaged membrane. The processed agent is thus trapped within the microorganism. One of ordinary skill in the art appreciates that a large number of substances can be used in the methods of this invention, e.g., calcein AM which is processed in the cytosol to free calcein, BCECF AM and other fluorescein diacetate derivatives. Presence of the processed agent in the culture medium is indicative of membrane damage. (See also, e.g., Corteses, "Death Watch 1: Cytotoxicity Detection," *The Scientist*, 15(5):26 (Mar. 5, 2001) and *Handbook of Fluorescent Probes and Research Chemicals*, Molecular Probes, Inc., 7$^{th}$ Edition, both incorporated herein by reference)

Numerous types of microorganisms can be used in the methods of this invention, such as, e.g., protozoa, gram positive bacteria, gram negative bacteria and fungus. Preferably the microorganism is an infective stage protozoa. More preferably, the microorganism is a sporozoite, a tachyzoite, or an epimastigote. Examples of suitable protozoa include, e.g., an *Eimeria* species, e.g., an *Eimeria acervulina* or *Eimeria tenella*, a *Toxoplasma* species, e.g., a *Toxoplasma gondii*, a *Crithidia* species, e.g., a *Crithidia fasciculata* or a *Trypanosoma* species, e.g., a *Trypanosoma cruzi*. Preferably the microorganism is an *Eimeria* species, particularly *Eimeria acervulina* or *Eimeria tenella*.

The methods of this invention are suitable for assaying a plurality of peptides, such as, e.g., a library of peptides, simultaneously for those with antimicrobial activity. Examples of libraries that can be assayed with a method of the present invention include a combinatorial chemistry library, a phage display library presenting the peptides on their surface, or a synthetic peptide library. With the use of a phage display library, a skilled artisan can easily isolate the nucleic acid molecule that encodes for the peptide that binds to the microorganism. Particular examples of phage libraries useful in the methods of the present invention include, but certainly are not limited to M13-derived phage libraries, e.g. the Ph.D.-7 and Ph.D.-C7C or Ph.D.12 libraries (New England Biolabs).

It is an object of the present invention to provide isolated peptides that possess antimicrobial activity. Preferably, the peptides are non-toxic, or are less toxic to host cells, e.g. animal or plant cells, as compared to heretofore known antimicrobial peptides, e.g., indolicidin and tritrpticin.

It is another object of the present invention to provide a method of isolating and assaying peptides for antimicrobial activity, and to use the antimicrobial peptides identified by these methods to inhibit infection of a host cell or to inhibit proliferation of the microorganism within an animal or plant, or to inhibit the viability, and proliferation of the microorganisms in an environment capable of supporting such viability and proliferation.

These and other aspects of the present invention will be better appreciated by reference to the following drawings and Detailed Description.

BRIEF DESCRIPTION OF THE DRAWINGS

FIG. 1. Deduced amino acid sequence of peptides identified after three rounds of selection of three peptide phage libraries. Only the peptides having amino acid sequences having the double tryptophan, i.e., "WW", motif are presented. The peptide sequences are aligned to preserve the relative position of the double tryptophan motif, which is indicated in boldface. Positively charged amino acids are indicated by grey boxes. The incidence column displays the frequency of each individual amino acid sequence in the total number of clones isolated and sequenced in each library. Sequences from top to bottom are SEQ ID NO: 1, 2, 3, 4, 5, 6, 7, 8, 9, 10, 11, 12, 13 and 14.

DETAILED DESCRIPTION OF THE INVENTION

Figure 2:
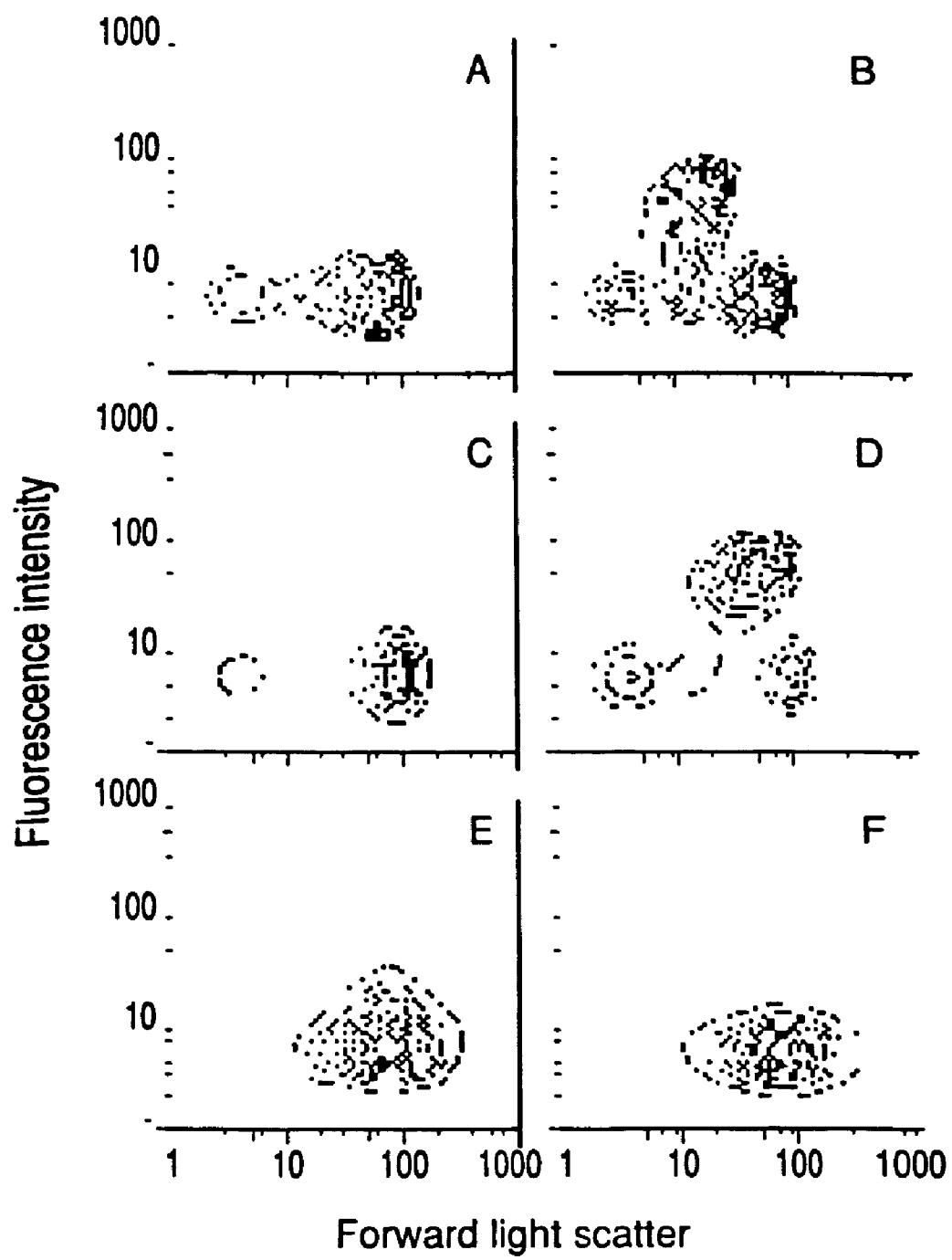
FIG. 2. Flow cytometry analysis data of PW2-treated and untreated E. acervulina and E. tenella sporozoites and C. fasciculata epimastigotes. Cells were incubated with the fluorescent dye Sytox Green (1:10,000) in the presence or absence of 100 ug/ml of PW2 peptide in HSBS for 15 minutes at 41° C. The experimental data is presented as a contour plot where the x-axis represents the forward light scatter, an indirect measure of cell size; whereas the y-axis represents the intensity of Sytox Green fluorescence, which is proportional to membrane permeability. (A, B) E. acervulina. (C, D) E. tenella. (E, F) C. fasciculata. (A,C,E) untreated cells. (B, D, F) PW2-treated cells.

Described herein is a method for identifying antimicrobial peptides by using a living infective stage of a microorganism, particularly a bacterium, a fungus or a protozoan parasite, to screen peptides. This method is particularly useful to identify antimicrobial peptides specific for Eimeria sporozoites.

The present invention relates to antimicrobial peptides consisting of about 10 to about 50 amino acids, preferably about 12 to about 45 amino acids, more preferably about 12 to about 35 amino acids and most preferably 12 to about 25 amino acids, wherein the peptide comprises 10 to 12 contiguous amino acids of which seven out of the 10 to 12 amino acids are hydrophobic, three out of the 10 to 12 contiguous amino acids are basic and at least one out of the 10 to 12 contiguous amino acid is histidine (His), glutamine (Glu) or serine (Ser), with the proviso that at least two of the seven hydrophobic amino acids are adjacent tryptophans (Trp). Preferably the peptide has an pI of about 10. Preferably the peptide comprises the amino acid sequence set forth in SEQ ID NO:1 or a conservative variant thereof. More preferably the peptide consists of the amino acid sequence set forth in SEQ ID NO: 1, referred to herein as "PW2."

PW2 has an amino acid composition that resembles the indolic peptides indolicidin and tritrpticin (Selsted et al., "Indolicidin, a novel tridecapeptide amide from neutrophils", J. Biol. Chem., 267:4292-4295 (1992); Lawyer et al., "Antimicrobial activity of a 13 amino acid tryptophan-rich peptide derived from a putative porcine precursor protein of a novel family of antibacterial peptides", FEBS Lett., 390:95-98 (1996)). Indolicidin and tritrpticin are peptides which are found in cytoplasmic granules of neutrophils and have a broad spectrum of activity against bacteria, fungi and protozoa; however, it has been demonstrated that indolicidin and tritrpticin are also hemolytic and cytotoxic (Ahmad et al., "Liposomal entrapment of the neutrophil-derived peptide indolicidin endows it with in vivo antifungal activity", Biochim. Biophys. Acta, 1237:109-114 (1995); Aley et al., "Killing of Giardia lamblia by cryptdins and cationic neutrophil peptides" Infect. Immun., 62 (12):5397-5403 (1994); Falla et al., "Mode of action of the antimicrobial peptide indolicidin", J. Biol. Chem. 271(32):19298-19303 (1996), and; Schibli et al., "Structure of the antimicrobial peptide tritrpticin bound to micelles: A distinct membrane-bound peptide fold", Biochemistry 38:16749-16755 (1999)). Their hemolytic and cytotoxic properties restrict the potential use of indolicidin and tritrpticin as therapeutic agents.

The PW2 peptide, which was identified using an infective stage of a protozoa, has minimal inhibitory effect upon the growth or proliferation of bacteria. PW2 however, showed significant activity against two avian Eimeria sporozoites, low activity against fungi and T. gondii tachyzoites, very low activity against T. cruzi, and no activity against C. fasciculata. This activity against Eimeria makes PW2 an excellent agent to prevent or treat avian coccidiosis. The peptide may be added to the feed to e.g., prevent proliferation of the Eimeria, or the peptide may be administered directly to the organism.

In contrast to indolicidin and tritrpticin, 100 ug/ml of PW2 showed no hemolytic effect against human, rabbit and chicken erythrocytes. Also, unlike indolicidin and tritrpticin, the PW2 peptide exhibits a low level of cytotoxic activity against mammalian and avian cells.

PW2 was identified and isolated as described infra. PW2 exhibits antimicrobial activity towards *Eimeria, Toxoplasma* and fungi comparable to that of known antimicrobial peptides, but with a much lower toxicity to host cells susceptible to infection by the microorganisms than is found with other antimicrobial peptides. Thus, PW2, along with analogs and conservative variants thereof, is useful for inhibiting the viability and proliferation of microorganisms, particularly sporozoites, in an environment that is capable of supporting such proliferation and viability. PW2 is also useful in compositions for treating an animal or plant in need thereof to prevent infection by the microorganism or to inhibit the proliferation and viability of the microorganism.

PW2 is particularly useful for inhibiting the growth of sporozoites, e.g., *Eimeria*, and fungi and does not appear to be particularly bacteriostatic or toxic to host cells. In addition, PW2's toxicity in mammalian cells is much lower than the toxicity of indolicidin and tritrpticin. Thus, in contrast to indolicidin and tritrpticin PW2 may be produced in large quantities in bacteria, e.g., *E. coli*, and in mammalian and plant cells.

Also an aspect of this invention are conservative variants of an isolated peptide comprising the amino acid sequence set forth in SEQ ID NO:1. The conservative variants of SEQ ID NO:1 comprise the two adjacent trytophans motif, WW, discussed previously. Those of skill in the art appreciate that certain amino acids may be substituted for other amino acids in a protein structure without appreciable loss of interactive capacity with structures such as, for example, substrate-binding regions.

These changes are termed "conservative" in the sense that they preserve the structural and the required functional qualities of the starting molecule. Conservative amino acid substitutions generally are based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape.

Figure 6:
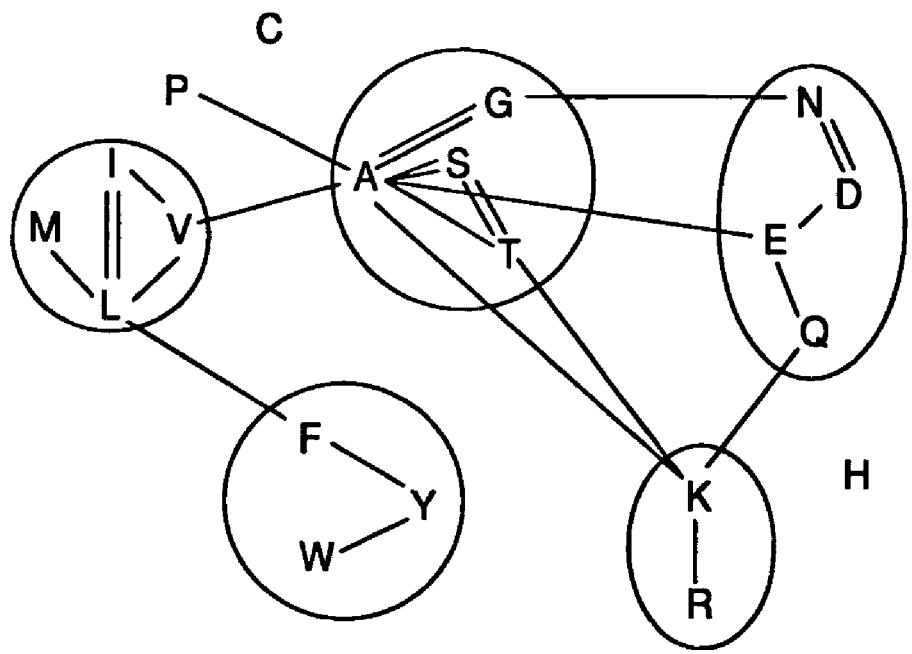
FIG. 6. Summary of rules for conservative amino acid substitutions (Bordo and Argos, JMB 217:721-729 (1991)). Amino acids connected by a solid line can be substituted with 95% confidence.

The importance of the effect of amino acid substitutions on the local and global folding of a polypeptide is generally understood in the art (see, e.g., Bordo & Argos, *J. Mol. Biol.*, 217:721-729 (1991); Jones, *J. Theor. Biol*, 50:167-183 (1975); Hoop and Woods, *Proc Natl Acad Sci USA* 78:3824 (1981) and Sweet & Eisenberg, *J Mol Biol* 171(4): 479-88 (1983)). For example, amino acid substitutions may introduce an amino acid with a particularly preferable property into the peptide. For example, a Cys maybe introduced at a potential site for a disulfide bridge with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure. Conservative substitutions by functionally equivalent residues can be performed based on charge and topological structure conservation. Conservative substitutions can be made according to the rules suggested by Bordo & Argos, supra. Bordo & Argos suggest certain amino acids may be substituted for other amino acids based on exchange matrices representing natural substitutions. The matrices were obtained by comparison of known conserved three-dimensional protein structures and the rules of substitution suggested by Bordo & Argos are set forth in FIG. 6.

One of ordinary skill in the art can make such substitutions chemically, or alternatively, produce a nucleic acid molecule which encodes a conservative variant of an isolated peptide comprising an amino acid sequence of SEQ ID NO:1 by using methods readily available to one of ordinary skill in the art, e.g., site-directed mutagenesis of an isolated nucleic acid molecule of the present invention followed by expression of the molecule, or by chemical synthesis.

Two designations for amino acids are used interchangeably throughout this application, as is common practice in the art. Alanine=Ala (A); Arginine=Arg (R); Aspartic acid=Asp (D); Asparagine=Asn (N); Cysteine=Cys (C); Glutamic acid=Glu (E); Glutamine=Gln (Q); Glycine=Gly (G); Histidine=His (H); Isoleucine=Ile (I); Leucine=Leu (L); Lysine=Lys (K); Methionine=Met (M); Phenylalanine=Phe (F); Proline—Pro (P); Serine=Ser (S); Threonine=Thr (T); Tryptophan=Trp (W); Tyrosine=Tyr (Y); Valine=Val (V).

Because of the degeneracy of the genetic code, a given polypeptide may be encoded by many nucleic acids. For example, four different three-base codons encode the amino acids alanine, glycine, proline, threonine and valine, while six different codons encode arginine, leucine and serine. Only methionine and tryptophan are encoded by a single codon. Table 1 lists the amino acids by name, three-letter and one-letter codes, and their corresponding codons for use in such embodiments.

TABLE 1

| Amino Acids | Code | Codons |
|---|---|---|
| Alanine | Ala | A GCA GCC GCG GCU |
| Cysteine | Cys | C UGC UGU |
| Aspartic acid | Asp | D GAC GAU |
| Glutamic acid | Glu | E GAA GAG |
| Phenylalanine | Phe | F UUC UUU |
| Glycine | Gly | G GGA GGC GGG GGU |
| Histidine | His | H CAC CAU |
| Isoleucine | Ile | I AUA AUC AUU |
| Lysine | Lys | K AAA AAG |
| Leucine | Leu | L UUA UUG CUA CUC CUG CUU |
| Methionine | Me | M AUG |
| Asparagine | Asn | N AAC AAU |
| Proline | Pro | P CCA CCC CCG CCU |
| Glutamine | Gln | Q CAA CAG |
| Arginine | Arg | R AGA AGG CGA CGC CGG CGU |
| Serine | Ser | S AGC AGU UCA UCC UCG UCU |
| Threonine | Thr | T ACA ACC ACG ACU |
| Valine | Val | V GUA GUC GUG GUU |
| Tryptophan | Trp | W UGG |
| Tyrosine | Tyr | Y UAC UAU |

Derivatives of an Isolated Peptide of the Present Invention.

The present invention also includes derivatives or analogs of an isolated peptide of the 30 present invention produced from a chemical modification. Analogs include isolated peptides of the present invention that are amidized, carboxymethylated or cyclized. One of ordinary skill in the art can readily produce such analogs using routine laboratory techniques.

An isolated peptide of the present invention may be derivatized by the attachment of one or more chemical moieties. The chemically modified derivatives may be further formulated for intraarterial, intraperitoneal, intramuscular, subcutaneous, intravenous, oral, nasal, pulmonary, topical or other routes of administration. Chemical modification of an isolated peptide of the present invention may provide additional advantages under certain circumstances, such as increasing stability, increasing membrane attachment and/or penetration, or increasing circulation time of the isolated peptide of the present invention, as well as decreasing its immunogenicity. See U.S. Pat. No. 4,179,337. For a review, see Abuchowski et al., in *Enzymes as Drugs* J. S. Holcerberg and J. Roberts, eds. pp. 367-383 (1981)incorporated herein by reference. A review article describing protein modification and fusion proteins is Francis, *Focus on Growth Factors* 3:4-10, Mediscript (1992): Mountview Court, Friem Barnet Lane, London N20, OLD, UK, incorporated herein by reference.

The chemical moieties suitable for derivatization may be selected from among water soluble polymers. The polymer selected should be water soluble so that an isolated peptide of the present invention does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations.

Examples of water soluble polymers having applications herein include, but are not limited to, polyethylene glycol, copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), dextran, poly(n-vinyl pyrrolidone)polyethylene glycol, propropylene glycol homopolymers, polypropylene oxide/ethylene oxide co-polymers, polyoxyethylated polyols or polyvinyl alcohol. Polyethylene glycol propionaldenhyde may have advantages in manufacturing due to its stability in water.

There are a number of attachment methods available to those skilled in the art, e.g., EP 0 401 384herein incorporated by reference (coupling PEG to G-CSF), see also Malik, *Exp. Hematol.*, 20:1028-1035 (1992) (reporting pegylation of GM-CSF using tresyl chloride)(incorporated herein by reference).

Furthermore, the present invention relates to a method of using a microorganism, particularly a pathogenic microorganism, to screen peptides for those which bind to the microorganism and then assaying those peptides for antimicrobial activity. Once it is determined which peptides cause damage to the microorganism, the sequence of the peptides maybe determined and the peptides maybe produced in sufficient quantities for use as agents to inhibit the proliferation and viability of the microorganism in an environment capable of supporting the proliferation and viability of the microorganism. The peptides may be produced in sufficient quantities and purity for use as a therapeutic agent to treat an animal or plant in need thereof by preventing or inhibiting microbial infection or proliferation.

Methods for Screening Peptides for Antimicrobial Activity

The present invention extends to a method for using a microorganism for screening a peptide for antimicrobial activity, comprising the steps of:
  (a) contacting one or more peptides with a microorganism for a time sufficient to permit binding of the peptides to the microorganism;
  (b) isolating the bound peptide from the microorganism; and
  (c) assaying the peptide for its ability to damage the microorganism wherein damage to the microorganism is indicative of antimicrobial activity of the peptide. Methods of examining the microorganism for damage are described infra.

In one embodiment a microorganism is contacted with an peptide to be assayed, thereafter the microorganism is assayed for damage to its surface, or cellular membranes. The microorganism may be examined after removal of the peptide for damage to the cellular membranes of the microorganism. Damage to the membranes caused by the peptide is indicative of the peptide's antimicrobial properties. Numerous methods of examining membranes are readily available to the skilled artisan, and may be used herein. One such method is a physical inspection with a microscope or an electron microscope.

Another method in accordance with the invention is to contact the microorganisms, which have been contacted with the peptide, with an agent that has affinity for a compound located within the microorganism, but is not able to cross an intact or undamaged membrane. Finding such an agent within the microorganism indicates that the agent crossed the membrane into the interior of the microorganism and that the membrane of the microorganism was damaged by the peptide. An example of such an agent is Sytox green dye (Molecular Probes, Eugene, Oreg.). This dye has a strong affinity for nucleic acids, but can only penetrate cells that have a damaged membrane. Alternatively, one may assay the culture medium surrounding the microorganism for a protein normally found within the microorganism but not normally in the culture medium. Finding the protein in the medium is indicative of damage to the microorganism. The protein may be detected using an antibody. Preferably, such an antibody is detectably labeled.

Yet another method for determining whether a peptide being assayed for antimicrobial activity has damaged the membrane of the microorganism involves contacting the microorganism after removal of the bound peptide with an agent that is able to cross the membrane of the microorganism and is processed within the microorganism to form a product that is unable to cross an undamaged membrane. The medium surrounding the microorganism is then assayed for the presence of the product. The finding of the product in the medium, where such a product should not normally be found, is indicative of damage to the membrane of the microorganism caused by peptide, and is indicative of the antimicrobial activity of the compound. An example of such an agent/product is calcein AM/free calcein. Calcein AM is converted into free calcein within the microorganism. Normally, free calcein is unable to cross the microorganism's membrane and enter the surrounding culture. Thus, detection of free calcein in the medium surrounding the microorganism is indicative of damage to the microorganism's membrane, and thus the antimicrobial activity of the peptide.

Any type of microorganism presently known or subsequently discovered may be used in the methods of the present invention e.g., a fungus, a sporozoite parasite, a gram positive bacterium or a gram negative bacterium. This method is particularly useful with an infective stage of a protozoa or fungus.

Moreover, the methods of the present invention are readily amendable to high throughput screening (HTS) in order to shorten the time scale for identifying peptides that have antimicrobial activity. In one embodiment, peptides are prepared and then a "combinatorial chemical libraries" containing a large number of potential therapeutic peptides are screened in one or more assays, as described herein, to identify those library members (particular chemical species or subclasses) that display a desired characteristic activity. The peptides thus identified can serve as conventional "lead peptides" in obtaining peptides having antimicrobial activity, or alternatively, can themselves be used as potential or actual therapeutics in the treatment and prevention of microbial infection in an animal or a human.

Combinatorial Chemical Libraries

Combinatorial chemical libraries are one type of library that can assist in the generation of new chemical compound leads. A combinatorial chemical library is a collection of diverse chemical compounds generated by either chemical synthesis or biological synthesis by combining a number of chemical "building blocks" such as amino acids. For example, a linear combinatorial chemical library, such as a peptide library, is formed by combining a set of amino acids in every possible combination for a peptide of a predetermined length. Millions of chemical compounds can be synthesized through such combinatorial mixing of chemical building blocks. Preparation and screening of combinatorial chemical libraries are well known to those of skill in the art. Such combinatorial chemical libraries include, but are not limited to peptide libraries (see, e.g., U.S. Pat. No. 5,010,175; Furka, *Int. J. Pept. Prot. Res.*, 37: 487-493 (1991), and; Houghton et al., *Nature*, 354: 84-88 (1991) incorporated herein by reference).

Solid phase peptide synthesis is not the only method available for producing peptides. Other methods known in the art for generating peptide libraries can also be used.

Another example of a library that has applications herein is a phage display library. In this type of library, nucleotide sequences encoding particular peptides are inserted into bacteriophage genomes. These phages then express the nucleotide sequences, and the resulting peptides are presented upon the surfaces of the phage. This type of library was utilized in the following example to identify an antimicrobial peptide of the present invention. Phage display libraries useful in this invention include, e.g., Ph.D.-7, Ph.D.-C7C, and Ph.D-12 (New England BioLabs, Cambridge Mass.); however, any phage display library presently known or subsequently discovered can be used in a method of the present invention.

The present invention also relates to a method for inhibiting viability, growth or spread of a pathogenic microorganism in an environment capable of supporting such growth, comprising administering an effective amount of the isolated peptide, a polytope of the peptide, or a conservative variant thereof or a polytope of such variants to the environment. An "effective amount" of the peptides of the present invention is an amount sufficient to inhibit the proliferation of the microorganism by at least about 30 percent, more preferably by at least 50 percent, even more preferably by at least 90 percent, and most preferably, to eradicate the microorganism from the environment. This invention also relates to preventing a microbial infection or inhibiting microbial proliferation and spread in a plant or animal in need thereof, comprising administering an effective amount of a peptide of the present invention or conservative variant thereof to the plant or animal. An "effective amount" of the peptide of the present invention is an amount sufficient to inhibit the infection or proliferation of the microorganism in the animal or plant. The methods of this invention are particular suited for inhibiting the viability, proliferation and spread of a fungus, e.g. *Candida albicans* or *Aspergillus nidulans*, as well as protozoa, particularly sporozites of, e.g., *Eimeria acervulina* and *Eimeria tenella*.

There are numerous application for the present invention, such as treatment of a water sample, a food product, an animal feed, a plant, an animal, e.g, a human or a bird and so forth. Indeed, the invention is useful in any situation in which it is desirable to inhibit microbial growth, such as the treatment of a microbial infection, has applications in a method of the present invention. For example, a peptide of the present invention can be readily administered to a water supply, a food product, an animal feed or crops, simply by adding the peptide to the water supply, food product, animal feed or crops. The peptide may be added to a water supply, a food product, animal feed or administered to an animal or plant with a suitable carrier in e.g., a solid, liquid, gel, foam or aerosol form.

In the case of an animal or a human, numerous methods of administering an effective amount of an isolated peptide of the present invention or a conservative variant thereof are available for use by the skilled artisan. Such isolated peptides may be introduced topically, parenterally, transmucosally, e.g., orally, nasally, or rectally, or transdermally, intra-arteriolely, intramuscularly, intradermally, subcutaneously, intraperitoneally, intraventricularly, and intracranially. Such administration can also occur via bolus administration. Oral solid dosage forms are described generally in Remington's Pharmaceutical Sciences, 18th Ed.1990 (Mack Publishing Co. Easton Pa. 18042) at Chapter 89, and; Marshall, K. In: *Modern Pharmaceutics* Edited by G. S. Banker and C. T. Rhodes Chapter 10, 1979, both incorporated herein by reference. A method and composition for pulmonary delivery of drugs for systemic effect is described in U.S. Pat. No. 5,451,569, issued Sep. 19, 1995 to Wong et al. (incorporated herein by reference). Systems of aerosol delivery, such as the pressurized metered dose inhaler and the dry powder inhaler are disclosed in Newman, S. P., *Aerosols and the Lung*, Clarke, S. W. and Davia, D. editors, pp. 197-22 and can be used in connection with the present invention.

In another embodiment, an isolated peptide of the present invention, or variant thereof, can be delivered in a vesicle, in particular a liposome (see Langer, *Science* 249:1527-1533 (1990); Treat et al., in *Liposomes in the Therapy of infectious Disease and Cancer*, Lopez-Berestein and Fidler (eds.), Liss: New York, pp. 353-365 (1989); Lopez-Berestein, ibid., pp. 317-327; see generally ibid.).

In yet another embodiment, a peptide of the present invention, or variant thereof, can be delivered in a controlled release system. For example, the peptide may be administered using intravenous infusion, an implantable osmotic pump, a transdermal patch, liposomes, or other modes of administration. In one embodiment, a pump may be used (see Langer, supra; Sefton, *CRC Crit. Ref Biomed. Eng.*, 14:201 (1987); Buchwald et al., *Surgery*, 88:507 (1980); Saudek et al., *N. Engl. J Med.*, 321:574 (1989)). In another embodiment, polymeric materials can be used (see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., Ann. Neurol. 25:351 (1989); Howard et al., *J. Neurosurg.* 71:105 (1989)). Other controlled release systems are discussed in the review by Langer (*Science* 249:1527-1533 (1990)).

Thus, the methods and pharmaceutical compositions of the present invention are particularly suited to administration to any animal, particularly a mammal or bird, including, but by no means limited to, domestic animals, such as feline or canine subjects, farm animals, such as, but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use. Particular examples of methods for administering an effective amount of an isolated peptide of the present invention, or conservative variant thereof, are described below.

Pharmaceutical Compositions

In another aspect of the present invention, provided herein are pharmaceutical compositions comprising isolated peptides of the present invention, or conservative variants thereof, and pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of an isolated peptide of the present invention, or conservative variant thereof. See, e.g., *Remington's Pharmaceutical Sciences*, 18th Ed. (1990, Mack Publishing Co., Easton, Pa. 18042) pages 1435-1712 which are herein incorporated by reference. The compositions may be prepared in liquid form, or may be in dried powder, such as lyophilized form.

Nucleic Acid Molecules

This invention also relates to nucleic acid molecules that encode isolated peptides of this invention, i.e., antimicrobial peptide consisting of about 10 to about 50 amino acids, preferably about 12 to about 45 amino acids, more preferably about 12 to about 35 amino acids and most preferably 12 to about 25 amino acids, wherein the peptide comprises 10 to 12 contiguous amino acids of which seven out of the 10 to 12 amino acids are hydrophobic, three out of the 10 to 12 contiguous amino acids are basic and at least one out of the 10 to 12 contiguous amino acid is histidine (His), glutamine (Glu) or serine (Ser), with the proviso that at least two of the seven hydrophobic amino acids are adjacent tryptophans (Trp). Preferably the nucleic acid molecules encode peptides that comprise the amino acid sequence of SEQ ID NO:1, or a conservative variant thereof. More preferably the nucleic acid molecule encodes a peptide consisting of an amino acid sequence set forth in SEQ ID NO:1, or a conservative variant. The invention also relates to cloning and expression vectors comprising the nucleic acid molecules and to host cells containing the nucleic acid molecules and vectors.

A "vector" is a replicon, such as a virus, plasmid, phage or cosmid, to which another DNA segment may be attached so as to bring about the replication of the attached segment. A "replicon" is any genetic element (e.g., plasmid, chromosome, virus) that functions as an autonomous unit of DNA, i.e., capable of replication under its own control.

A DNA "coding sequence" is a double-stranded DNA sequence which is transcribed and translated into a peptide or polypeptide in a cell in vitro or in vivo when placed under the control of appropriate regulatory sequences. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence can be located 3' to the coding sequence.

Transcriptional and translational control sequences are DNA regulatory sequences, such as promoters, enhancers, terminators, and the like, that provide for the expression of a coding sequence in a host cell.

A "promoter sequence" or "promoter" is a DNA regulatory region capable of binding RNA polymerase in a cell and initiating transcription of a downstream (3' direction) coding sequence. The promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then spliced and translated into the protein encoded by the coding sequence.

A coding sequence is "in operable association with" or "operable linkage with" a transcriptional and translational control sequences, such as, for example, a promoter when RNA polymerase transcribes the coding sequence into mRNA, which in turn is translated into a protein encoded by the coding sequence.

This invention also relates to nucleic acid molecules encoding isolated peptides of this invention, particularly isolated nucleic acid molecules encoding peptides comprising the amino acid sequence of SEQ ID NO:1, or a conservative variant thereof. Due to the degenerate nature of the genetic code as discussed supra, an isolated peptide of the present invention can be encoded by a large number of isolated nucleic acid molecules.

The present invention further relates to cloning vectors and expression vectors comprising an isolated nucleic acid molecule of this invention, which can be introduced into a cell where it can be replicated. Vectors include, e.g., plasmids, cosmids, viruses (bacteriophage, animal viruses and plant viruses), and artificial chromosomes. One of skill in the art appreciates that a vector may be constructed using methods that are well known and readily available in the art (see, for example, Sambrook and Russell, Molecular Cloning: A Laboratory Manual (Third Edition)(2001) Cold Spring Harbor Laboratory Press, Cold Spring Harbor, N.Y., and F. M. Ausubel et al. (eds.), *Current Protocols in Molecular Biology*, John Wiley & Sons, Inc. (1994), both incorporated by reference). Any of the methods readily available to those of skill in the art for the insertion of nucleic acid molecules into a vector may be used to construct expression vectors of the present invention. These methods include, e.g., in vitro recombinant DNA and synthetic techniques and in vivo recombination (genetic recombination). The vector elements controlling transcription and translation vary in their strengths and specificities. Depending on the host-vector system utilized, any one of a number of suitable transcription and translation elements may be used. The nucleic acid molecule may encode a single peptide or a polytope as described supra.

An isolated nucleic acid molecule of the present invention may be expressed extrachromosomally or chromosomally, after integration of the nucleic acid molecule into a host cell genome by recombination. In this regard, any of a number of amplification systems maybe used to achieve high levels of stable gene expression (See Sambrook, Fritsch & Maniatis, *Molecular Cloning: A Laboratory Manual*, Second Edition (1989) Cold Spring Harbor Laboratory Press, Cold Spring Harbor, N.Y.), e.g., mammalian cell systems containing a virus (e.g., vaccinia virus, adenovirus, etc.); insect cell systems infected with virus (e.g., baculovirus); microorganisms such as, e.g., yeast containing a yeast vector; or bacteria transformed with bacteriophage, DNA, plasmid DNA, or cosmid DNA, or; plant cells infected with *A. tumefaciens*, or *A. rhizogenes*, or transfected with a plasmid, wherein all the vectors comprise the isolated nucleic acid molecules of this invention.

In one embodiment, an isolated nucleic acid molecule of the present invention is inserted into an appropriate cloning vector in order to produce multiple copies of the isolated nucleic acid molecule. A large number of vector-host systems known in the art may be used are suitable for this invention. Possible vectors include, but are not limited to, plasmids or modified viruses. The vector system must be compatible with the host cell. Examples of suitable vectors include, but are not limited to, bacteriophages, e.g., lambda phage, or plasmids, e.g., derivatives of pBR322 or pUC, e.g., pGEX vectors, pMal-c, pFLAG, etc.

Any of the methods readily available to those of skill in the art for the insertion of nucleic acid molecules into a vector may be used to construct cloning and expression vectors of the present invention. These methods include, e.g., in vitro recombinant DNA and synthetic techniques and in vivo recombination (genetic recombination). The insertion into a cloning vector can, for example, be accomplished by ligating an isolated nucleic acid molecule of the present invention into a cloning vector which has complementary cohesive termini. If the restriction sites used to digest the cloning vector are not complementary to the ends of the isolated nucleic acid molecule being inserted therein however, the ends of either vector or the isolated nucleic acid molecule of the present invention may be enzymatically modified. Alternatively, any site desired may be produced by ligating nucleotide sequences (linkers) onto the DNA termini. These ligated linkers may comprise specific chemically synthesized oligonucleotides encoding restriction endonuclease recognition sequences. In an alternative method, an isolated nucleic acid molecule of the present invention may be identified and isolated after insertion into a suitable vector in a "shot gun" approach. Enrichment for the isolated nucleic acid molecule, for example, by size fractionation, can be done before insertion into the vector.

Such recombinant molecules can then be introduced into host cells via transformation, transfection, infection, electroporation, etc., so that many copies of an isolated nucleic acid molecule of the present invention can be generated.

The vector may be a shuttle vector, which is a vector that can replicate in more than one type of host cell. The shuttle vector provides for expansion of vector copy number in a cell, e.g., *E. coli*, and facile purification of the vector in large quantities for subsequent introduction into an appropriate cell line for expression, if such is desired. For example, a shuttle vector can be prepared for replication in both *E. coli* and *Saccharomyces cerevisiae* by linking sequences from an *E. coli* plasmid with sequences from the yeast 2µ plasmid.

Another aspect of this invention relates to expression vectors comprising an isolated nucleic acid molecule of this invention in operable linkage with a promoter. Appropriate expression vectors contain the necessary elements for the transcription and translation of the inserted nucleic acid molecule. Suitable promoters include, e.g. an immediate early promoter of CMV, an early promoter of SV40, an early promoter of adenovirus, an early promoter of vaccinia, an early promoter of polyoma, a late promoter of SV40, a late promoter of adenovirus, a late promoter of vaccinia, a late promoter of polyoma, a lac promoter system, a trp promoter system, a TAC promoter system, a TRC promoter system, a promoter of lambda phage, an fd coat protein promoter, a 3-phosphoglycerate kinase promoter, an acid phosphatase promoter or a yeast α mating factor promoter, a promoter which is functional in plants, e.g., a glutelin-1 promoter, a califlower mosaic virus promoter, e.g. a 35S CaMV promoter, or a low molecular weight promoter, etc.

The invention further relates to host cells comprising the isolated nucleic acid molecules of this invention and to host cells comprising the expression vectors of this invention. Particular host cells include, but are not limited to, a bacterial cell, e.g., *E. coli, Pseudonomas, Bacillus*, yeast cells, e.g., *Streptomyces*, mammalian cells, e.g., CHO, R1.1, B-W, L-M, COS1, COS7, BSC1, BSC40, BMT10, Sf9, or NIH3T3 cells, insect cells, e.g., beet army worm cells, or plant cells, e.g., dicotyledonous cells, e.g., tobacco, tomato, potato or sugarcane, or monocotyledonous cells, e.g., amaranth, maize, oat, rice, wheat or sorghum.

Expression of an isolated nucleic acid molecule of the present invention may be controlled by any promoter/enhancer element known in the art, provided these regulatory elements are functional in the host cell selected for expression. Promoters which may be used to control expression include, but are not limited to, the SV40 early promoter region (Benoist and Chambon, 1981, *Nature* 290:304-310), the promoter contained in the 3' long terminal repeat of Rous sarcoma virus (Yamamoto, et al., *Cell*, 22:787-797 (1980)), the herpes thymidine kinase promoter (Wagner et al., *Proc. Natl. Acad. Sci. U.S.A.*, 78:1441-1445 (1981)), the regulatory sequences of the metallothionein gene (Brinster et al., *Nature*, 296:39-42 (1982)); prokaryotic expression vectors such as the β-lactamase promoter (Villa-Kamaroff et al., *Proc. Natl. Acad. Sci. U.S.A.*, 75:3727-3731 (1978)), or the tac promoter (DeBoer et al., *Proc. Natl. Acad. Sci. USA.*, 80:21-25 (1983); see also "Useful proteins from recombinant bacteria" in *Scientific American*, 242:74-94 (1980)); promoter elements from yeast or other fungi such as the Gal 4 promoter, the ADC (alcohol dehydrogenase) promoter, PGK (phosphoglycerol kinase) promoter, alkaline phosphatase promoter. Animal transcriptional control regions, which exhibit tissue specificity, have been utilized in transgenic animals: elastase I gene control region which is active in pancreatic acinar cells (Swift et al., *Cell*, 38:639-646 (1984); Ornitz et al., *Cold Spring Harbor Symp. Quant. Biol.*, 50:399-409 (1986); MacDonald, *Hepatology* 7:425-515 (1987)); insulin gene control region which is active in pancreatic beta cells (Hanahan, *Nature* 315:115-122 (1985)), immunoglobulin gene control region which is active in lymphoid cells (Grosschedl et al., *Cell* 38:647-658 (1984); Adames et al., *Nature* 318:533-538 (1985); Alexander et al., *Mol. Cell. Biol.*, 7:1436-1444) (1987), mouse mammary tumor virus control region which is active in testicular, breast, lymphoid and mast cells (Leder et al., *Cell*, 45:485-495 (1986)), albumin gene control region which is active in liver (Pinkert et al., *Genes and Devel.*, 1:268-276 (1987)), alpha-fetoprotein gene control region which is active in liver (Krumlauf et al., *Mol. Cell. Biol.*, 5:1639-1648 (1985); Hammer et al., *Science*, 235:53-58 (1987)), alpha 1-antitrypsin gene control region which is active in the liver (Kelsey et al., *Genes and Devel.*, 1:161-171 (1987)), beta-globin gene control region which is active in myeloid cells (Mogram et al., *Nature* 315:338-340 (1985); Kollias et al., *Cell*,46:89-94 (1986)), myelin basic protein gene control region which is active in oligodendrocyte cells in the brain (Readhead et al., *Cell*, 48:703-712 (1987)), myosin light chain-2 gene control region which is active in skeletal muscle (Sani, *Nature*, 314:283-286 (1985)), and gonadal releasing hormone gene control region which is active in the hypothalamus (Mason et al., *Science*, 234:1372-1378 (1986)).

Promoters for plant specific expression are known to those of skill in the art, and include but are not limited to, any constitutive, inducible, tissue or organ specific, or developmental stage specific promoter which can be expressed in the particular plant cell and include viral, synthetic, constitutive as described (Poszkowski et al., *EMBO J.*, 3:2719, 1989; Odell et al., *Nature*, 313:810-812, 1985), temporally regulated, spatially regulated, and spatio-temporally regulated (Chau et al., *Science*, 244:174-181, 1989). Those of skill in the art appreciate that the appropriate promoter will depend on the system being used for expression of the nucleic acid molecules.

Promoters suitable for use herein include, but are not limited to, at least one regulatory sequence from the T-DNA of *A. tumefaciens*, including mannopine synthase, nopaline synthase, and octopine synthase; alcohol dehydrogenase promoter from corn; light inducible promoters such as ribulose-biphosphate-carboxylase small subunit gene from a variety of species and the major chlorophyll a/b binding protein gene promoter; the maize ubiquitin promoter and intron (U.S. Pat. No. 5,510,474); the wheat low molecular weight glutenin promoter (Colot et al., *EMBO J,* 6: 3559-3564 (1987)) or the glutelin-1 promoter, histone promoters (EP 507 698), actin promoters; maize ubiquitin 1 promoter (Christensen et al., *Transgenic Res.*, 5:213 (1996)); 35S and 19S promoters of cauliflower mosaic virus (Gardner et al., *Nucl. Acids Res.*, 9: 2871-2888 (1981)); developmentally regulated promoters such as the waxy or bronze promoters from maize or prolamin promoters from maize, sorghum or Coix (Leite et al., *Mol. Breeding*, 6:47-63 (2000)); as well as synthetic or other natural promoters which are either inducible or constitutive, including those promoters exhibiting organ specific expression or expression at specific development stage(s) of the plant, e.g., the alpha-tubulin promoter disclosed in U.S. Pat. No. 5,635,618, all the foregoing promoter references are incorporated herein by reference.

This invention also relates to a method for producing the peptides of the present invention. In one embodiment, a host cell comprising a nucleic acid molecule, or an expression vector, of this invention is cultured under conditions that provide for production of one or more of the peptides of this invention. The peptides are then obtained from the host cells, the culture supernatant, or both.

The vectors may also comprise a marker gene e.g., β-glucuronidase, β-galactosidase, phosphomannose-isomerase, neomycin phosphotransferase II, hygromycin phosphotransferase and phosphinothricin acetyl transferase, which confers a selectable or screenable phenotype, e.g., resistance to antibiotics and herbicides. The vectors may also comprise a marker gene that provides for a transformation phenotype, occlusion body formation in baculovirus, etc.

A wide variety of host cell/expression vector combinations may be employed in expressing the nucleic acid molecules of this invention. Useful expression vectors, for example, may comprise segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., *Gene* 67:31-40 (1988)), pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2μ plasmid or derivatives thereof. Suitable vectors also include vectors useful in eukaryotic cells, such as, e.g., baccufovirus or cosmids and vectors derived from combinations of plasmids and phage DNAs, such as plasmids that have been modified to employ phage DNA or other expression control sequences; and the like.

For example, in a baculovirus expression systems, both non-fusion transfer vectors, such as butnot limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors provide for coamplification, e.g. those comprising dihydrofolate reductase (DHFR) gene and the nucleic acid molecule of interest; see Kaufman, *Current Protocols in Molecular Biology,* 16.12 (1991), or e.g., a glutamine synthetase/methionine sulfoximine co-amplification vector, such as pEE14 (HindIII, XbaI, SmaI, SbaI, EcoRI, and BclI cloning site, in which the vector expresses glutamine synthase and the nucleic acid molecule of interest; Celltech) can be used. In another embodiment, a vector that directs episomal expression under control of Epstein Barr Virus (EBV) can be used, such as pREP4 (hivitrogen), pCEP4 (Invitrogen), pMEP4 (Invitrogen), pREP8 (Invitrogen), pREP9 (Invitrogen), and pEBVHis (Invitrogen).

Other vectors include selectable mammalian expression vectors e.g., pRc/CMV (Invitrogen), pRc/RSV (Invitrogen), and others. Vaccinia virus mammalian expression vectors (see, Kaufman, 1991, supra) for use according to the present invention include but are not limited to pSC11, pMJ601, and pTKgptF1S.

Yeast expression systems can also be used according to the present invention to produce an isolated peptide of this invention. For example, the non-fusion pYES2 vector (Invitrogen) or the fusion pYESHisA, B, C (Invitrogen), to mention just two, can be employed according to the invention.

Examples of host cells of the present invention include, but are not limited to, bacteria, e.g., *E. coli, Pseudonomas, Bacillus,* yeast cells, e.g., *Streptomyces* and *Saccharomyces*, mammalian cells, e.g., CHO, R1.1, B-W, L-M, COS1, COS7, BSC1, BSC40, BMT10 and Sf9 cells, avian cells or plant cells, e.g., the plant cells maybe dicotyledonous, such as, e.g., tobacco, tomato, ornamentals, potato, rapeseed, sugarcane, soybean, cotton, canola, alfalfa and sunflower, or monocotyledonous plant cells, such as, e.g., amaranth, barley, maize, millet, oat, rice, rye, sorghum, tuffgrass or wheat cells.

In addition, a host cell may be chosen which modulate the expression of the isolated nucleic acid molecule such that the resulting peptide having specificity for a pathogenic microorganism and having antimicrobial activity is modified and processed as desired. Different host cells have characteristic and specific mechanisms for the traslational and post-translational processing and modification (e.g., glycosylation, cleavage (e.g., of signal sequence)) of peptides. Appropriate cell lines or host systems can be chosen to ensure the desired modification and processing of the foreign peptide expressed. For example, expression in a bacterial system can be used to produce an nonglycosylated core peptide product. However, a translocation signal sequence ligated to an isolated nucleic acid molecule of the present invention may not be properly spliced. Expression in yeast can produce a glycosylated product. Expression in mammalian cells can provide a tool for reconstituting, or constituting activity of the nucleic acid molecule. Furthermore, different vector/host expression systems may affect processing reactions, such as proteolytic cleavages, to a different extent.

Vectors may be introduced into the desired host cells by methods known in the art, e.g., transfection, electroporation, microinjection, transduction, cell fusion, DEAE dextran, calcium phosphate precipitation, liposome mediated DNA uptake, particle or microprojectile bombardment, or a DNA vector transporter, a disarmed Ti-plasmid vector carried by Agrobacterium exploiting its natural gene transfer ability or by silicon carbide fiber mediated transformation and other forms of direct DNA uptake (see, e.g., Wu et al., *J. Biol. Chem.*, 267:963-967 (1992); Wu and Wu, *J. Biol. Chem.*, 263:14621-14624 (1988); Hartmut et al., Canadian Patent Application No. 2,012,311, filed Mar. 15, 1990; EP-A-270355; EP-A-0116718; NAR, 12(22) 8711-87215 (1984); U.S. Pat. No. 5,100,792; EP-A-444882; EP-A-434616; WO 92/09696; WO 94/00583; EP 331083; EP 175966; Green et al., *Plant Tissue and Cell Culture*, Academic Press (1987); EP 290395; WO 8706614; DE 4005152; WO 9012096; U.S. Pat. No. 4,684,611; Freeman et al., *Plant Cell Physiol.*, 29: 1353 (1984); Kindle, *PNAS U.S.A.*, 87: 1228 (1990); Physical methods for the transformation of plant cells are reviewed in Oard, *Biotech. Adv.*, 9: 1-11(1991) all incorporated herein by reference.)

An isolated peptide of the present invention produced as an integral membrane protein can be isolated and purified by standard methods. Generally, the peptide can be obtained by lysing the membrane with detergents, such as, but not limited to, sodium dodecyl sulfate (SDS), TRITON X-100, nonidet P-40 (NP-40), digoxin, sodium deoxycholate, and the like, including mixtures thereof Solubilization can be enhanced by sonication of the suspension. Soluble forms of an isolated peptide of the present invention can be obtained by collecting culture fluid, or solubilizing inclusion bodies, e.g., by treatment with detergent, and if desired, sonication or other mechanical processes, as described above. The solubilized or soluble peptide can be isolated using various techniques, such as polyacrylamide gel electrophoresis (PAGE), isoelectric focusing, 2-dimensional gel electrophoresis, chromatography (e.g., ion exchange, affinity, immunoaffnity, and sizing column chromatography), centrifugation, differential solubility, immunoprecipitation, or by any other standard technique for the purification of proteins.

Antibodies to an Isolated Peptide of the Present Invention

Also included in the present invention are antibodies specific for an isolated peptide of this invention, preferably a peptide comprising an amino acid sequence of SEQ ID NO:1 or a conservative variant thereof. Such antibodies could be used for example to detect the binding of the peptides to a microorganism or to isolate and purify the peptides. Such antibodies include, but are not limited to, polyclonal, monoclonal, chimeric, single chain Fv fragments, Fab fragments, and an Fab expression library. Various procedures known in the art maybe used for the production of polyclonal antibodies to an isolated peptide of the present invention, a conservative variant thereof. For the production of an antibody, various animals can be immunized by injection with an isolated peptide of the present invention or conservative variant thereof, including, but not limited to rabbits, mice, rats, sheep, goats, etc. In one embodiment, an isolated peptide of the present invention or a conservative variant thereof can be conjugated to an immunogenic carrier, e.g., bovine serum albumin (BSA) or keyhole limpet hemocyanin (KLH). Various adjuvants may be used to increase the immunological response depending on the host species, including, but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies of the present invention, any technique that provides for the production of antibody molecules by continuous cell lines in culture may be used. These include but are not limited to the hybridoma technique originally developed by Kohler and Milstein (*Nature* 256:495-497 (1975) incorporated herein by reference), as well as the trioma technique, the human B-cell hybridoma technique (Kozbor et al., *Immunology Today* 4:72 (1983); Cote et al., *Proc. Natl. Acad. Sci. U.S.A.* 80:2026-2030 (1983) both incorporated herein by reference), and the EBV-hybridoma technique to produce human monoclonal antibodies (Cole et al., in *Monoclonal Antibodies and Cancer Therapy*, Alan R. Liss, Inc., pp. 77-96 (1985) incorporated herein by reference). In an additional embodiment of the invention, monoclonal antibodies can be produced in animals utilizing recent technology (PCT/US90/02545). In fact, according to the invention, techniques developed for the production of "chimeric antibodies" (Morrison et al., *J. Bacteriol.* 159:870 (1984); Neuberger et al., *Nature* 312:604-608 (1984); Takeda et al., *Nature* 314:452-454(1985) both incorporated herein by reference) by splicing the genes from a mouse antibody molecule specific for a peptide or polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the present invention, techniques described for the production of single chain antibodies (U.S. Pat. No. 4,946,778; incorporated herein by reference) can be adapted to produce single chain antibodies specific for an isolated peptide of the present invention or a conservative variant thereof. An additional embodiment of the invention utilizes the techniques described for the construction of Fab expression libraries (Huse et al., *Science* 246:1275-1281 (1989) incorporated herein by reference) to allow rapid and easy identification of monoclonal Fab fragments with the desired specificity for an isolated peptide of the present invention or conservative variant thereof.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc.

An isolated peptide of the present invention, an antibody specific for an isolated peptide of the present invention, or an isolated nucleic acid molecule which encodes an isolated peptide of the present invention, may be labeled or conjugated with a conjugation partner. Suitable labels and conjugation partners include, e.g., radioisotopes, e.g., $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$, fluorophores (e.g., fluorescene isothiocyanate (FITC), phycoerythrin (PE), Texas red (TR), rhodamine, free or chelated lanthanide series salts, especially $Eu^{3+}$), chromophores, chelating agents, enzymes, dyes, colloidal gold, latex particles, ligands (e.g., biotin), and chemiluminescent agents.

Radioisotopes such as, e.g., $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are known and those of skill in the art appreciate that there are many methods useful for labeling peptides, antibodies and nucleic acid molecule and for determining the presence of the label. Likewise one of skill in the art is familiar with a variety of techniques for the formation of a conjugate between a peptide and a conjugation partner, e.g., an enzyme, which are applicable to the peptides and nucleic acids of this invention. Those of skill in the art are also familiar with a variety of techniques for assaying for the conjugate, e.g., colorimetric, spectrophotometric, fluorospectrophotometric, amperometric or gasometric techniques known in the art.

Direct labels are one example of labels which can be used according to the present invention. A direct label is readily visible, either to the naked eye, or with the aid of an optical filter and/or applied stimulation, e.g., U.V. light to promote fluorescence. Examples include colored labels e.g., metallic particles, for example, gold particles such as those described by Leuvering (U.S. Pat. No. 4,313,734); dyes, such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70, 419-439(1980) and in U.S. Pat. No. 4,857,453.

Other labels for use in the invention include magnetic beads or magnetic resonance imaging labels. These detectable labels have applications in labeling an isolated peptide of the present invention or conservative variant, an antibody of the present invention, or an isolated nucleic acid molecule that encodes an isolated peptide of the present invention, or conservative variant thereof.

Furthermore, in accordance with the present invention there may be employed conventional molecular biology, microbiology, and recombinant DNA techniques within the skill of the art. Such techniques are explained fully in the literature. See, e.g., Sambrook et al., 1989; DNA Cloning: *A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994), all incorporated herein by reference.

The following examples are presented in order to more fully illustrate the preferred embodiments of the invention. They should not be construed in any manner as limiting the broad scope of the invention.

EXAMPLE 1

A. Microorganism Strains.

*E. acervulina* and *E. tenella* oocysts were obtained by passage in 4-5 week old 'hy-line' chickens (Long et al., "A guide to laboratory techniques used in the study and diagnosis of avian coccidiosis", *Fol. Veter. Lat.* 6:201-217 (1976) incorporated herein by reference). Sporozoites were purified using anion-exchange chromatography (Schmatz et al., "Purification of *Eimeria* sporozoites by DE-52 anion exchange chromatography", *J. Protozool.* 31:181-183 (1984) incorporated herein by reference). *T. gondii* tachyzoites were obtained from intraperitoneal exudates of infected white mice (*Mus musculus*) by washing with phosphate buffered solution, pH 7.2 (Robert et al., "Purification of *Toxophasma gondii* suspensions from mice peritoneal exudate", *Biomed. Pharmacol.* 36:98-100 (1982) incorporated herein by reference). *C. fasciculata* and *T. cruzi* epimastigotes were cultivated in LIT medium at 30° C. (Camargo, "Growth and differentiation in *Trypanosoma cruzi*. I Origin of metacyclic trypanosomes in liquid media", *Rev. Inst. Med. Trop. S. Paulo* 6:93-100 (1964) incorporated herein by reference).

EXAMPLE 2

A. Peptide Selection Of The Phage-display Libraries.

Three different M13-derived phage display peptide libraries were used for the selection of sporozoite-binding phage (Phage-Display Peptide Library Kits Ph.D.-7, Ph.D.-C7C, and Ph.D.-12 (New England BioLabs, Cambridge, Mass.)). Two of these libraries (Ph.D.-7 and Ph.D.-C7C) display 7-mer random peptides fused to the pIII M13 coat protein. In the C7C library the randomized sequence is flanked by a pair of cysteine residues that allow the display of cyclized version of the peptides. The third phage display peptide library, Ph.D.-12 displays 12-mer random peptides.

*E. acervulina* sporozoites ($1 \times 10^{8}$ cells) were incubated for 1 hour with $2 \times 10^{11}$ phage from each Ph-D library in 1 ml of TBS buffer (50 mM Tris-HCl, 150 mM NaCl, 5 mg/ml BSA, pH 7.5) containing 5 mg/ml of bovine serum albumin (BSA). The unbound phage particles were removed by washing six times with TBS/BSA. The specific bound phage particles were then eluted by incubation with 1 ml of 0.2 M Glycine buffer, pH 2.2, containing 1 mg/ml BSA, for 10 minutes at room temperature. The eluated fractions were neutralized with 150 ul of 1 M Tris, pH 9.0. *E. coli* ER2537 was infected with the recovered phage, the infected *E. Coli* was cultured under conditions which permitted replication of the phage and the phage was then partially purified by precipitation with polyethylene glycol using standard techniques. After titration, the eluted phage were subjected to two additional binding/amplification cycles. After the third cycle, DNA of individual phage clones was sequenced using standard techniques.

DNA sequencing of phage recovered after three rounds of selection revealed a peptide motif containing two tryptophan residues (FIG. 1) "WWmotif", found in 67%, 73% and 92% of the sequenced antimicrobial peptides isolated from the phage of the Ph.D-7, -C7C and -12 libraries, respectively. Furthermore, an arginine or lysine residue often follows the WW motif. HPLKQYWWRPSI (SEQ ID NO:1), named PW2, was chosen for further studies.

PW2 contains seven hydrophobic amino acids and three basic amino acids and has an estimated isoeletric point of 10. The "WW" motif is shared with two natural antimicrobial peptides, indolicidin (ILPWLWPWWPWRR) (SEQ ID NO:2) (Selsted et al., *J. Biol. Chem.*, 267:4292-4295 (1992) and tritrpticin (VRRFPWWWPFLRR) (SEQ ID NO:3) (Lawyer et al., *FEBS Lett.*, 390:95-98 (1996) incorporate herein by reference) having estimated isoelectric points of 12.6 and 12.1 respectively.

B. PW2 Peptide Synthesis

An automated bench-top simultaneous multiple solid-phase peptide synthesizer PSSM 8 System (Shimadzu, Japan) was used for the solid-phase synthesis of the peptide by the Fmoc-procedure. The peptides were deprotected in TFA and purified by semipreparative HPLC using an Econosil C-18 column (10 μ, 22.5×250 mm). The molecular mass and purity of synthesized peptides were checked by MALDI-TOF mass spectrometry TofSpec-E, confirming that the peptides of interest had been synthesized.

EXAMPLE 3

A. Sporozoite Membrane Permeabilization Activity of PW2 Peptide.

The effect of PW2 upon the membrane permeability of *Eimeria* sporozoites, *E. acervulina* and *E. tenella*, and an unrelated parasite, *Crithidia fasciculata*, were initially studied by means of flow cytometry, specifically, sporozoites were incubated with 100 ug/ml of PW2 for 15 minutes at 37° C. in 10 mM HEPES, pH 7.2 buffer containing 0.25 M sucrose (HSBS) and Sytox Green diluted 10,000 fold. Sytox Green dye has a strong affinity for nucleic acids, but can only penetrate cells that have a damaged membrane.

Flow cytometric measurements were performed in a FacStar Plus model (Becton-Dickinson, Franklin Lakes, N.J.) using standard methods. The argon laser excitation was set at 488 nm. Fluorescence emission was determined using a 530 nm (green) band-pass filter, and the results were analyzed with CellQuest software (Becton-Dickinson, Franklin Lakes, N.J.).

Cell size, measured as forward light scatter, and membrane integrity were correlated in a contour plot (FIG. 2). Sporozoites of *E. acervulina* and *E. tenella* were compared with epimastigotes of an unrelated parasite, *Crithidia fasciculata* (Trypanosomatidae). The treated cells were separated into three different groups. The group having the smallest cell volume (lowest forward light scatter) displayed a very low fluorescence intensity and represent cell debris, while the group having low fluorescence intensity byt the largest volume (highest forward light scatter) represents intact cells. The third group of cells had an intermediate volume and the highest fluorescent intensity indicative of cell permeabilization with concomitant volume reduction. The number of particles from the distinct groups were counted by flow cytometry and used to calculate percentages.

After a short exposure (15 minutes), strong damage was observed on both *E. acervulina* and *E. tenella*, while *Crithidia fasciculata* was not affected. The percentage of injured cells in the presence or absence of peptide was 62% and 20% for *E. acervulina* and 82% and 10% for *E. tenella* sporozoite populations, respectively. These results indicate that the sporozoites of *E. tenella* are more sensitive to PW2 than those of *E. acervulina*, but both were sensitive to the peptide.

Figure 3A:
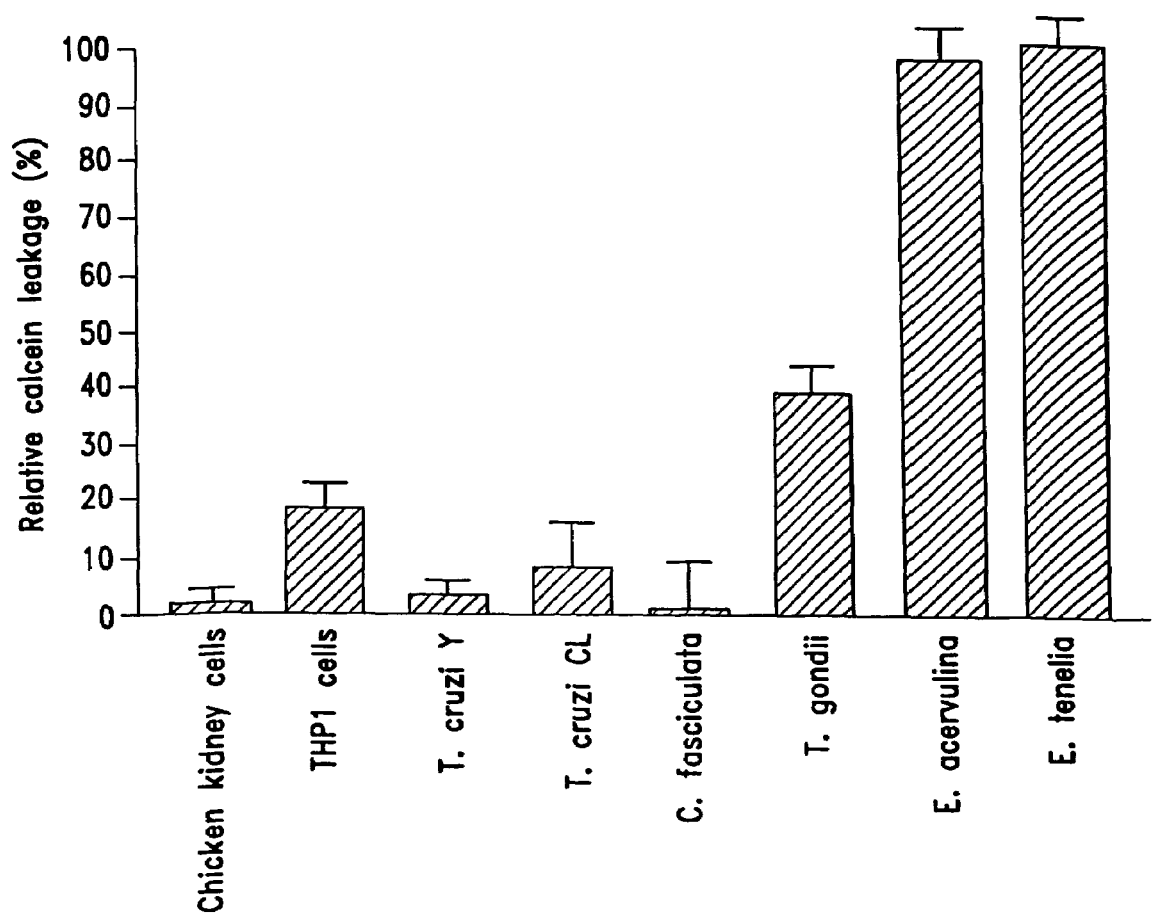
FIGS. 3A, 3B and 3C. Effect of PW2 in calcein leakage. (A) Calcein leakage induced by incubation with 100 ug/ml of PW2 for 1 hour at 37° C. is presented as percentage of the fluorescence intensity obtained in experiments using 0.2% of TRITON X-100. The fluorescence intensity obtained in control experiments with buffer solution was discounted in all assays. (B) and (C) Time course of calcein leakage from E. acervulina and E. tenella sporozoites ($10^6$), respectively, induced by different concentrations of PW2 at 37° C. All the assays were performed in triplicate using $10^6$ cells. The bars represent standard deviations.

Membrane permeability was also studied by means of a calcein leakage assay based upon uptake by cells of Calcein-AM. Calcein-AM (a non-fluorescent ester) readily crosses cell membranes and is processed by cytosolic esterases, to form a fluorescent product (free calcein). As the cell membrane is impermeable to free calcein, any treatment that affects cell integrity releases the trapped fluorescent product. After sedimentation of cells and debris the probe can be detected in the supernatant by fluorimetry. This approach was used to evaluate the effect of PW2 upon sporozoites of *E. acervulina, E. tenella*, tachyzoites of *Toxoplasma gondii*, and epimastigotes of *Crithidia fasciculata* and *Trypanosoma cruzi*. The effects of PW2 on human lymphoma THP1 and primary chicken kidney cultured cells was also assayed (FIG. 3A).

Cells were incubated with 1 uM Calcein-AM (Molecular Probes, Eugene, Oreg.) in HSBS for 2 hours at 37° C. The parasites, chicken kidney cells ($1 \times 10^6$ cells), and THP1 human lymphoma cells ($1 \times 10^6$ cells) were incubated in 150 ul HSBS containing PW2 (100 ug/ml) for 1 hour at 37° C. After incubation, cell suspensions were centrifuged at low speed (1,000×g for 3 min) and 100 ul of supernatants were recovered and diluted to 1 ml in Milli-Q water. The THP1 human lymphoma cells used in this assay were cultivated in RPMI medium supplemented with 10% fetal calf serum, in 5% $CO_2$ atmosphere at 37° C. The fluorescence of free calcein in the surrounding medium was measured in a spectrofluorimeter set at 490 nm for excitation and 530 nm for emission.

Figure 3B:
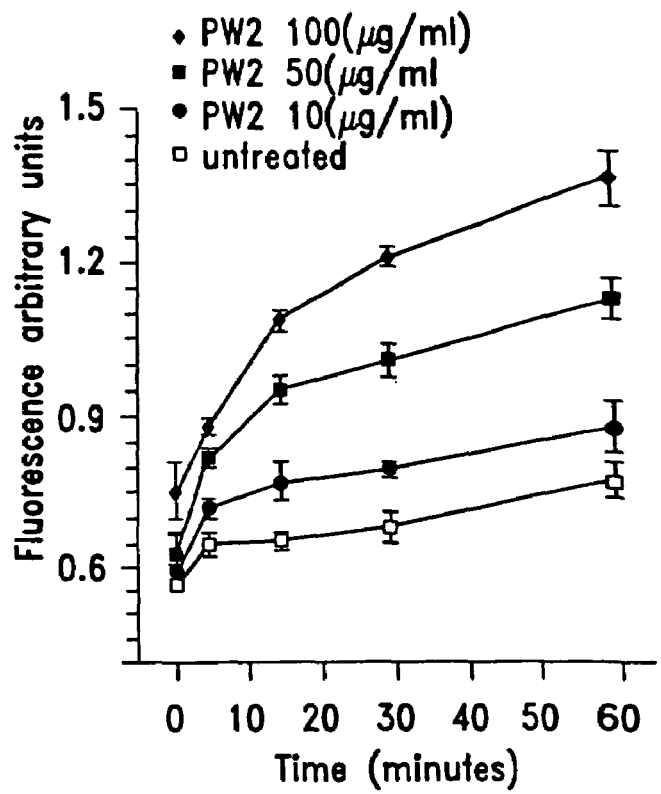
Figure 3C:
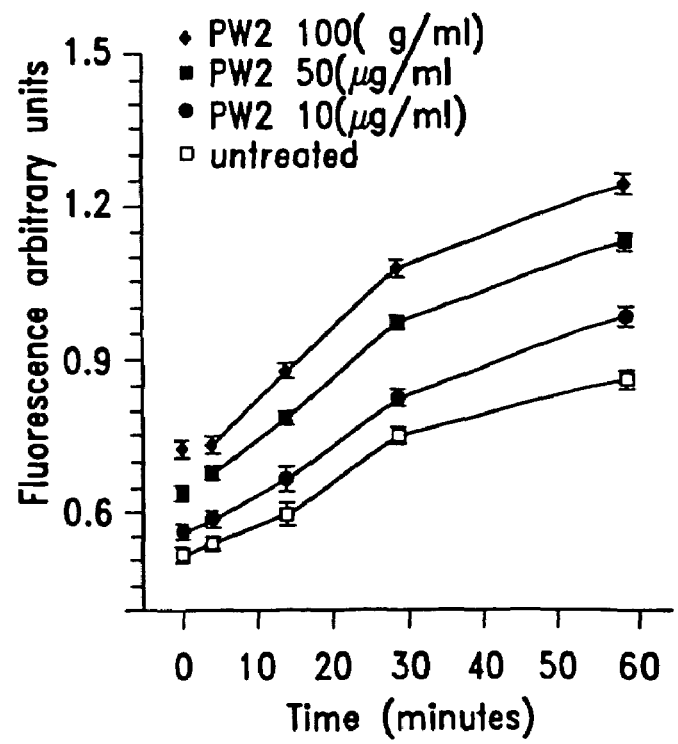
Figure 4A:
FIG. 4. Scanning electron microscopy of PW2-treated and untreated E. acervulina sporozoites. Sporozoites were incubated with PW2 peptide for 1 hour at 41° C. in HSBS. Progressive damage of the sporozoite surface membrane and increase in cell debris as well as cell fusion can be observed with higher concentrations of PW2 peptide. (A, C) untreated. (D) PW2 1 ug/ml. (E) PW2 10 ug/ml. (F) PW2 50 ug/ml. (B, G, H) PW2 100 ug/ml.
Figure 4B:
Figure 4C:
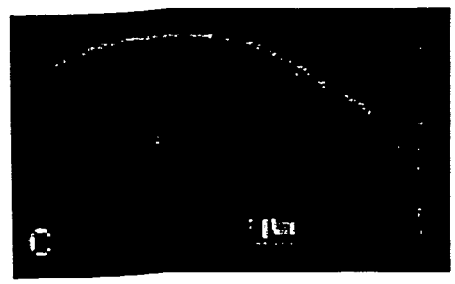
Figure 4D:
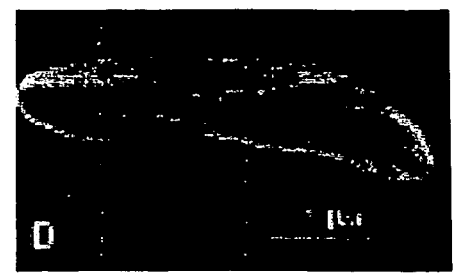
Figure 4E:
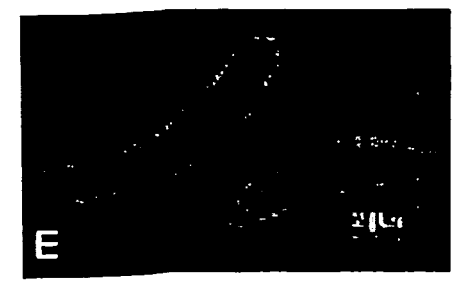
Figure 4F:
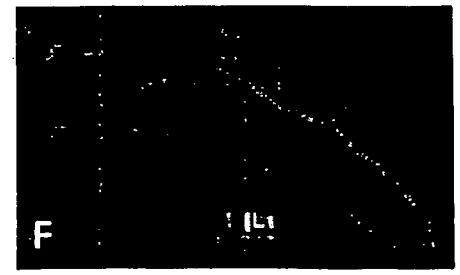
Figure 4G:
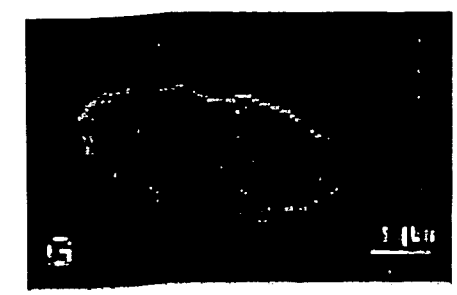
Figure 4H:

The percentage of calcein leakage was compared to standards, i.e., the fluorescence intensity of cells treated with 0.2% Triton™ X-100 (100% calcein leakage) and the fluorescence intensity of cells treated with buffer alone (baseline calcein leakage, 0% ). PW2 showed insignificant effect on chicken kidney cells and upon the unrelated protozoans *C. fasciculata* and *T. cruzi* (Mastigophora) and some effect (38.4% calcein leakage) on the closely related protozoa *T. gondii*. The effect of PW2 on THP1 cells was low (18% calcein leakage); however, the same treatment caused 97.4% and 100% effect on *E. acervulina* and *E. tenella* sporozoites, respectively. Kinetic assays of the calcein leakage from sporozoites showed that the effect of peptide depends on its concentration (FIGS. 3B and 3C). The difference in the patterns observed could reflect differences in membrane composition between the two *Eimeria* species.

B. Scanning Electron Microscopy

Freshly purified sporozoites of *E. acervulina* ($10^5$ cells) were incubated in 50 ul HSBS, 41° C., for 1 hour in the absence or presence of PW2 (1, 10, 50 and 100 ug/ml). After incubation, 10 ul aliquots were separated for scanning electron microscopy. The sporozoiites were deposited on cover slips during five minutes decantation and fixed for ten minutes in 0.1 M phosphate buffer, pH 7.6, containing 2.5% glutaraldehyde. After dehydration in alcohol, cells were processed in a Balzer CPD 30 critical point dryer. Cover slips were attached with carbon tape on stubs and gold sputtered for two minutes. Cell surface images were obtained via scanning electron microscopy.

Images of *E. acervulina* sporozoites treated for 1 hour showed progressive surface damage and cell debris as the concentration of peptide increased (FIG. 4). At high peptide concentrations (50 and 100 ug/ml) the injured cells formed aggregates (FIGS. 4B and 4H) and showed partial loss of cytoplasm (FIGS. 4F and 4G). This indicates that the increase in sporozoite permeabilization results from the disruption of the sporozoite membrane induced by the PW2 peptide.

C. Effect of PW2 Peptide Upon Sporozoite Cell-invasion.

The effect of PW2-peptide upon the viability of Eimeria sporozoites was investigated by measuring invasion by sporozoites of primary chick kidney cultured cells.

Primary chick kidney cells (one day-old chick kidney cells) were cultivated on round cover slips in polyethylene plates with 24 wells ($5 \times 10^5$ cells/well) in 1 ml Eagle 199 medium containing 10% fetal calf serum and 1% penicillin/streptomycin for 72 hours at 37° C., 5% $CO_2$ to produce semi-confluent monolayers (Doran, "Increasing the yield of *Eimeria tenella* oocysts in cell culture", *J. Parasitol,* 57:891-900 (1971) (incorporated herein by reference)).

*E. acervulina* and *E. tenella* sporozoites were pre-treated for one hour at 41° C. with 1, 10, 50 and 100 ug/ml PW2 in 1 ml HSBS and were rinsed three times for peptide removal in HSBS.

Pre-treated sporozoites of *E. acervulina* ($1.5 \times 10^6$/well) and *E. tenella* ($5 \times 10^5$) were added to the primary chick kidney cells cultured on cover slips (six replicates for *E. acervulina* and in triplicate for *E. tenella*) and were incubated at 41° C. for four hours with 5% $CO_2$. The number of cell-invading sporozoite were then determined by treating the chick kidney cells with methanol for 10 minutes and staining with Giemsa solution (1:50 w/v) for one hour. One hundred microscopic fields ($\times 1{,}000$ magnification) were examined under a light microscope and the number of cell-invading sporozoites were counted. Sporozoites treated with 1 ug/ml of PW2 showed a significant reduction in ability to invade cells compared with untreated sporozoites (Table 2 as determined by one-way analysis of variance using the PROC GLM programme of SAS Institute (SAS Institute Inc. SAS/STATIM User's guide, Release 6.03 Edition, Cary, N.C.: SAS Institute Inc., 1028 pp (1988)incorporated herein by reference).

TABLE 2

Inhibitory effect of PW2 peptide on the invasion of *E. acervulina* and *E. tenella* sporozoites in chicken cultured cells.

| Table 2 | Number of intracellular sporozoites | | | |
|---|---|---|---|---|
| | *E. acervulina* | | *E. tenella* | |
| PW2 peptide | Mean number* | Percentage | Mean number* | Percentage |
| 1 | 35.3$^b$ | 27.6% | 88.8$^b$ | 22.5% |
| 10 | 25.8$^c$ | 20.2% | 84.2$^b$ | 21.3% |
| 50 | 24.8$^c$ | 19.4% | 63.9$^{b,c}$ | 16.2% |
| 100 | 24.5$^c$ | 19.2% | 36.3$^c$ | 9.2% |
| Untreated | 127.8$^a$ | 100% | 394.8$^a$ | 100% |

*Mean number of intracellular sporozoites counted in 100 microscopic fields with magnification $\times$ 1,000. One-way ANOVA analysis: variables followed by at least one similar letter did not differ significantly when Duncan's multiple range test was used (overall error rate a = 0.05).

A reduction of approximately 70% in the number of sporozoites able to invade cell for both *Eimeria* species was observed. Inhibition of cell invasion at higher peptide concentrations (10, 50 and 100 ug/ml) increased to about 80% for *E. acervulina* and 90% for *E. tenella* with no significant differences for PW2 concentrations above 10 ug/ml in both species.

EXAMPLE 4

A. The Specificity of PW2 Antimicrobial Activity

The antimicrobial activity of PW2 was tested against bacteria and fungi. The Minimum Inhibitory Concentration (MIC) of PW2 against fungi and bacteria were determined by monitoring liquid growth inhibition in 1.2% Potato Dextrose Broth medium (fungi) or Peptone Broth medium (bacteria) using two times serial dilutions of peptide (Ehret-Sabatier et al., "Characterization of novel cysteine-rich antimicrobial peptides from scorpion blood", *J. Biol. Chem.,* 271:29537-29544 (1996) incorporated herein by reference). MICs were expressed as the (a)-(b) interval of concentrations, where (a) is the highest concentration in which growth was observed and (b) is the lowest concentration that causes 100% of growth inhibition.

Concentrations up to 200 ug/ml have no antibacterial effect against Gram-positive *Micrococcus luteus* and *Staphylococcus aureus* and Gram-negative *Escherichia coli*; Howerver, PW2 had an inhibitory effect upon the growth of the fungi *Candida albicans* and *Aspergillus nidulans* with a minimum inhibitory concentration (MIC) of 12.5-25 and 25-50 ug/ml, respectively. PW2 also displayed an activity against other phytopathogenic fungi as shown in Table 3:

TABLE 3

PW2 Antimicrobial Activity

| Phytopathogenic fungi | PW2 MIC | Host Plant |
|---|---|---|
| *Colletotrichum gossypii var. cephalosporioides* | 50-100 ug/ml (31-62 uM) | cotton |
| *Alternaria macrospora* | 12.5-25 ug/ml (7.75-15.5 uM) | cotton |
| *Bipolaris sorokiniana* | 50-100 ug/ml (31-62 uM) | wheat |
| *Dreschslera tritici* | 50-100 ug/ml (31-62 uM) | wheat |
| *Phoma sorghina* | 50-100 ug/ml (31-62 uM) | rice |
| *Microdochium oryzae* | 50-100 ug/ml (31-62 uM) | rice |
| *Bipolaris oryzae* | 25-50 ug/ml (15.5-31 uM) | rice |
| *Pyricularia grisea* | 50-100 ug/ml (31-62 uM) | rice |
| *Colletotrichum gloeosporioides* | 50-100 ug/ml (31-62 uM) | mango, avocado, fig, guava, papaya, onion, cassava, orange, eggplant, pimento, rubber tree |
| *Rhizoctonia solani* | 100-200 ug/ml (62-124 uM) | lettuce |
| *Fusarium solani* | 25-50 ug/ml (15.5-31 uM) | beans |

B. Mode of Action of PW2 Peptide.

Tryptophan fluorescence was monitored on a spectrofluorimeter with excitation wavelength of 295 nm and emission scanned from 310 to 450 nm. Scans were taken with a 10 nm emission/excitation bandwidth and a scan speed of 40 nm/s. The PW2 concentration of 10 ug/ml in 1 ml of HSBS was used in the presence or absence of 25 mM SDS. For fluorescence quenching experiments, acrylamide was added from 8 M stock solution to final concentrations of 0.1 to 0.5 M. The emissions were analysed at 351 nm in the absence of SDS, and at 343 nm in the presence of SDS micelles. The fluorescence quenching constants ($K_{SV}$) for acrylamide, in the presence and absence of SDS, were determined using the Stem-Volmer equation (Eftink and Ghiron, "Exposure of tryptophanyl residues in proteins. Quantitative determination by fluorescence quenching studies", *Biochemistry,* 15:672-680 (1976) incorporated herein by reference). Right angle light scattering of PW2 in HSBS was monitored using a spectrofluorimeter by setting both excitation and emission at 500 m. All the fluorescence experiments were performed on a F-2000 Fluorescence Spectrophotometer (Hitachi, Japan).

Figures 5A, 5B, 5C:
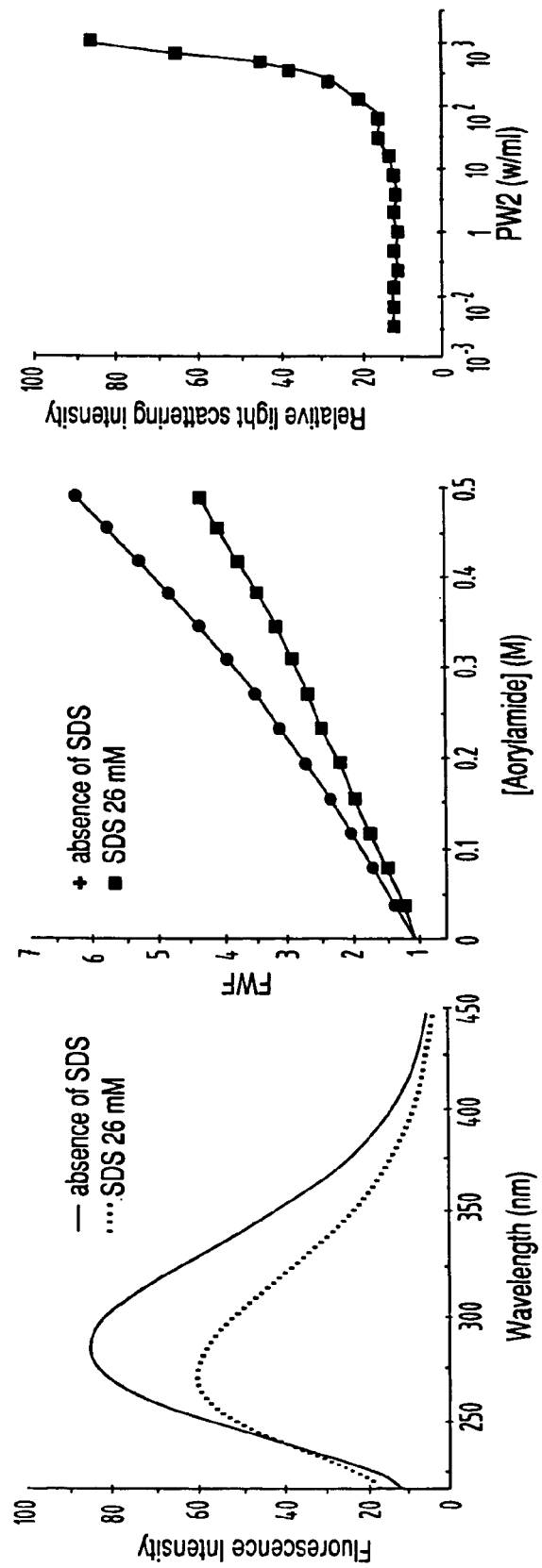
FIG. 5. (A) Fluorescence spectra of PW2 peptide in the absence (solid line) and presence (dashed line) of 25 mM SDS. Fluorescence emission peaks are at 351 and 343 mm in the absence and presence of SDS, respectively. (B) Acrylamide quenching analysis of PW2 in the absence (circle) and presence (square) of 25 mM SDS. Stem-Volmer calculated constants for PW2 are 10.8 $M^{-1}$ and 6.8 $M^{-1}$ in the absence and presence of 25 mM SDS, respectively. (C) Straight angle light scattering analysis of PW2 in HSBS. The amount of light scattered was measured using a fluorescence spectrophotometer with excitation and emission wavelengths set at 500 mm.

Comparative analysis of fluorescence spectra of PW2 in the presence and absence of membrane-mimicking SDS micelles revealed a blue shift of 8 nm in the maximum emission peak from 351 to 343 nm (FIG. 5A). This blue shift denotes the displacement of tryptophan residues to the hydrophobic core of the SDS micelle. The partial burial of the PW2 tryptophan residues in the presence of SDS micelles was confirmed by acrylamide fluorescence quenching experiments. The Stem-Volmer constants ($K_{SV}$) for PW2 are 10.8 $M^{-1}$ and 6.8 $M^{-1}$ in the absence and presence of SDS, respectively (FIG. 5B). The $K_{SV}$ values indicate that tryptophan residues are more accessible to acrylamide when PW2 is free in the solution, corroborating with the partitioning of tryptophan residues into the hydrophobic core of micelles.

Since the activity of the antimicrobial peptide indolicidin depends on self association (Ahmad et al., *Biochim. Biophys. Acta* 1237, 109-114 (1995) incorporated herein by reference), the aggregation of PW2 was investigated. This was monitored by straight angle light scattering at increasing concentrations of PW2 peptide. FIG. 5C shows that the ability of PW2 to scatter 500 nm light increases considerably when its concentration reaches 100 ug/ml.

Membrane permeabilization has been proposed as the mechanism of indolicidin and tritrpticin antimicrobial activity (Falla et al., *J. Biol. Chem.*, 271(32): 19298-19303 (1996); Schibli et al., *Biochemistry,* 38:16749-16755 (1999) both incorporated herein by reference.) The composition similarity of these peptides and the results disclosed herein suggest a similar mode of action for PW2. The mechanism is based on insertion into the membrane by aromatic residues of the peptide that are then stabilised by interactions among basic residues of the peptide and negatively charged residues of the microbial membrane. The high frequency of the double-tryptophan motif (WW motif) among the selected peptides and the previous observation that trytophan residues can promote partitioning into lipid bilayer (Wimley & White, "Experimentally determined hydrophobicity scale for proteins at membrane interfaces", *Nat. Struct. Biol.,* 3:842-848 (1996)incorporated herein by reference) indicate that this motif plays an important role in the mechanism of antimicrobial activity. Light scattering experiments indicate that self-association of PW2 takes place at concentrations (50-100 μg/ml) that induce intense damage in the membrane of *E. acervulina* sporozoites. This suggests that the anticoccidial effect of PW2 is related to the formation of peptide aggregates. In contrast to indolicidin, the microbicide concentration of PW2 does not coincide with the onset of in vitro hemolytic activity. In vitro invasion experiments showed that sporozoite invasion is inhibited at lower concentrations and this may indicate that sporozoites gradually lose their viability before a lytic concentration is reached.

The results clearly demonstrated the potential use of phage display libraries to select pathogen-specific peptides and that this method and the peptides identified thereby may be exploited in the development of new antimicrobial drugs.

The methods described herein have identified a heretofore unknown peptide that is active against avian *Eimeria*. The peptide (HPLKQYWWRPSI) (SEQ ID NO:1), named PW2, shows anticoccidial activity against *Eimeria acervulina* and *Eimeria tenella* sporozoites in vitro and is also effective against fungi, e.g., *Candida albicans*. The peptide apparently acts by disrupting the sporozoite membrane. In addition, the PW2 peptide exhibits low toxicity to bacteria, mammalian and avian cells. As such the peptide maybe produced recombinantly in bacteria, mammalian and plant cells with little adverse effects on these cells and the peptide has applications as a therapeutic for preventing or inhibiting the viability, growth and proliferation of microorganisms in organisms that are susceptible to infection thereby, such as for example: mammals, e.g., humans, cats, dogs, hamsters, cows, pigs, sheep, horses; birds, e.g., chickens, doves, ducks, geese, pigeons and turkeys, and; plants, such as dicotyledonous plants, e.g., tobacco, tomato, ornamentals, potato, rapeseed, sugarcane, soybean, cotton, canola, alfalfa and sunflower, or monocotyledons plants, such as, e.g., amaranth, barley, maize, millet, oat, rice, rye, sorghum, tufgrass or wheat. The peptide also has applications for preventing or inhibiting the viability, growth and proliferation of the microorganism in environments that are capable of supporting the growth and proliferation of the microorganisms, e.g., water supplies, crops, food products and animal feed.

Any references cited herein are not and should not be taken as an acknowledgment or any form of suggestion or admission that the references are prior art to the invention described herein.

The present invention is not limited in scope by the specific embodiments described herein. Indeed, various modifications of the invention in addition to those described herein will become apparent to those skilled in the art from the foregoing description and the accompanying figures.

We claim:

1. An isolated antimicrobial peptide consisting of from 10 to 12 amino acids of which 7 out of said 10 to 12 amino acids are hydrophobic residues, 3 of said 10 to 12 amino acids are basic residues and at least one of said 10 to 12 amino acids is histidine (His), glutamic acid (Glu) or seine (Ser), with the proviso that two of the hydrophobic amino acids must be tryptophan (Trp) residues and said two tryptophan residues are adjacent tryptophans.

2. The isolated antimicrobial peptide of claim 1, comprising the amino acid sequence set forth in SEQ ID NO: 1.

3. The isolated antimicrobial peptide of claim 1, wherein said peptide is amidated, carboxyinethylated or cyclized.

4. The isolated peptide of claim 1, consisting of the amino acid sequence set forth in SEQ ID NO: 1, 2, 3, or 4.

5. A method for identifying an antimicrobial peptide which binds to an infective stage microorganism and damages said microorganism comprising:
    (a) contacting an infective stage microorganism with a plurality of non-identical peptides of claim 1,
    (b) identifying peptides that bind to the microorganism, and
    (c) assaying the peptides identified in (b) for capacity to damage the microorganism,
wherein damage to said microorganism by a peptide of (c) indicates that the peptide of (c) is an antimicrobial peptide which binds to an infective stage microorganism and damages said microorganism.

6. The method of claim 5, wherein the plurality of peptides is expressed on a bacteriophage.

7. The method of claim 5, comprising contacting said microorganism with a library of synthetic peptides.

8. The method of claim 1, wherein the microorganism is a protozoa, a fungus, a Gram positive bacterium or a Gram negative bacterium.

9. A method for preventing growth, inhibiting growth or decreasing viability of a microorganism comprising contacting said microorganism with an effective amount of the peptide of claim 1, sufficient to prevent growth, to inhibit growth or to decrease viability of said microorganism.

10. The method of claim 9, wherein said microorganism is a protozoa or a fungus.

11. The method of claim 10, wherein the protozoa is an *Eimeria* (*E.*) species, a *Toxoplasma* (*T.*) species, a *Crithidia* (*Cr.*) species, or a *Trypanosoma* (*Tr.*) species.

12. The method of claim 10, wherein the fungus is selected from the group consisting of *Candida albicans* or *Asperillus nidulans, Colletotrichum gossypii, Alternaria macrospora, Bipolaris sorokiniana, Dreschslera tritici, Phoma sorghina, Microdochium oryzae, Bipolaris oryzae, Pyricularia grisea, Colletotrichum gloeosporioides, Rhizoctonia solani* and *Fusarium solani*.

13. The method of claim 10, wherein the protozoa is selected from the group consisting of *E. acervulina* or *E. tenella*.

14. The method of claim 9, wherein said microorganism is present in an environment that is capable of sustaining viability of the microorganism.

15. The method of claim 14, wherein said environment is a water sample, a food product, a feed, an animal, or a plant.

16. A method for treating an organism infected with a pathogenic microorganism comprising administering an effective amount of the isolated antimicrobial peptide of claim 1 to said organism sufficient to alleviate said infection.

17. The method of claim 16, wherein said organism is a bird, a mammal, or a plant.

18. The method of claim 16, wherein the pathogenic microorganism is a fungus, or a protozoa.

19. The method of claim 18, wherein the protozoa is an *Eimeria*, or a *Toxoplasma*.

20. The method of claim 18, wherein the fungus is selected from the group consisting of *Candida albicans* or *Aspergillus nidulans, Colletotrichum gossypii, Alternaria macrospora, Bipolaris sorokiniana, Dreschslem tritiei, Phoma sorghina, Microdochium oryzac, Bipolaris oryzae, Pyricularia grisea, Colletotrichum gloeosporioides, Rhizoctonia solani* and *Fusarium solani*.

* * * * *

SEQUENCE LISTING

```
<160> NUMBER OF SEQ ID NOS: 14

<210> SEQ ID NO 1
<211> LENGTH: 12
<212> TYPE: PRT
<213> ORGANISM: Artificial sequence
<220> FEATURE:
<223> OTHER INFORMATION: This is a synthetic peptide.

<400> SEQUENCE: 1

His Pro Leu Lys Gln Tyr Trp Trp Arg Pro Ser Ile
1               5                   10

<210> SEQ ID NO 2
<211> LENGTH: 12
<212> TYPE: PRT
<213> ORGANISM: Artificial sequence
```

```
<220> FEATURE:
<223> OTHER INFORMATION: This is a synthetic peptide.

<400> SEQUENCE: 2

Pro Ile Trp Trp Lys His Ser Gly Gly Pro Ile Leu
1               5                   10

<210> SEQ ID NO 3
<211> LENGTH: 12
<212> TYPE: PRT
<213> ORGANISM: Artificial sequence
<220> FEATURE:
<223> OTHER INFORMATION: This is a synthetic peptide.

<400> SEQUENCE: 3

Tyr Trp Trp Arg Asp Ala Pro Val Ser Gln Gly Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: This is a synthetic peptide.

<400> SEQUENCE: 4

Ser Tyr Pro Thr Asp Lys Trp Trp Ile Lys Pro Gly
1               5                   10

<210> SEQ ID NO 5
<211> LENGTH: 7
<212> TYPE: PRT
<213> ORGANISM: Artificial sequence
<220> FEATURE:
<223> OTHER INFORMATION: This is a synthetic peptide.

<400> SEQUENCE: 5

Val Gln Trp Trp Arg Pro Thr
1               5

<210> SEQ ID NO 6
<211> LENGTH: 7
<212> TYPE: PRT
<213> ORGANISM: Artificial sequence
<220> FEATURE:
<223> OTHER INFORMATION: This is a synthetic peptide

<400> SEQUENCE: 6

Asn Trp Trp Arg Pro Leu Pro
1               5

<210> SEQ ID NO 7
<211> LENGTH: 7
<212> TYPE: PRT
<213> ORGANISM: Artificial sequence
<220> FEATURE:
<223> OTHER INFORMATION: This is a synthetic peptide.

<400> SEQUENCE: 7

Gly Lys Trp Trp Val Phe Asp
1               5

<210> SEQ ID NO 8
<211> LENGTH: 7
<212> TYPE: PRT
<213> ORGANISM: Artificial sequence
<220> FEATURE:
```

-continued

```
<223> OTHER INFORMATION: This is a synthetic peptide.

<400> SEQUENCE: 8

Val Pro Thr Lys Pro Trp Trp
1               5

<210> SEQ ID NO 9
<211> LENGTH: 7
<212> TYPE: PRT
<213> ORGANISM: Artificial sequence
<220> FEATURE:
<223> OTHER INFORMATION: This is a synthetic peptide.

<400> SEQUENCE: 9

Pro Trp Trp Lys Thr Ser Lys
1               5

<210> SEQ ID NO 10
<211> LENGTH: 7
<212> TYPE: PRT
<213> ORGANISM: Artificial sequence
<220> FEATURE:
<223> OTHER INFORMATION: This is a synthetic peptide.

<400> SEQUENCE: 10

Pro Trp Trp Lys Ala Ser Ser
1               5

<210> SEQ ID NO 11
<211> LENGTH: 7
<212> TYPE: PRT
<213> ORGANISM: Artificial sequence
<220> FEATURE:
<223> OTHER INFORMATION: This is a synthetic peptide.

<400> SEQUENCE: 11

Thr Pro Thr Trp Trp Arg Thr
1               5

<210> SEQ ID NO 12
<211> LENGTH: 7
<212> TYPE: PRT
<213> ORGANISM: Artificial sequence
<220> FEATURE:
<223> OTHER INFORMATION: This is a synthetic peptide.

<400> SEQUENCE: 12

Ala Pro Thr Trp Trp Lys Ser
1               5

<210> SEQ ID NO 13
<211> LENGTH: 7
<212> TYPE: PRT
<213> ORGANISM: Artificial sequence
<220> FEATURE:
<223> OTHER INFORMATION: This is a synthetic peptide.

<400> SEQUENCE: 13

Trp Trp Thr Ser Ala Ser Arg
1               5

<210> SEQ ID NO 14
<211> LENGTH: 8
<212> TYPE: PRT
<213> ORGANISM: Artificial sequence
<220> FEATURE:
<223> OTHER INFORMATION: this is a synthetic peptide.
```

```
<400> SEQUENCE: 14

Ser Ala Arg Trp Trp Gln Pro Ser
1               5
```